(12) United States Patent
Goulet et al.

(10) Patent No.: US 7,700,778 B2
(45) Date of Patent: Apr. 20, 2010

(54) ACYLATED PIPERIDINE DERIVATIVES AS MELANOCORTIN-4 RECEPTOR AGONISTS

(75) Inventors: Mark T. Goulet, Westfield, NJ (US); Ravi P. Nargund, East Brunswick, NJ (US); Feroze Ujjainwalla, Scotch Plains, NJ (US); Thomas F. Walsh, Watchung, NJ (US); Daniel Warner, Stoneham, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 1142 days.

(21) Appl. No.: 11/239,770

(22) Filed: Sep. 30, 2005

(65) Prior Publication Data

US 2006/0025442 A1 Feb. 2, 2006

Related U.S. Application Data

(62) Division of application No. 10/468,517, filed as application No. PCT/US02/08002 on Feb. 25, 2002, now Pat. No. 7,012,084.

(60) Provisional application No. 60/272,259, filed on Feb. 28, 2001.

(51) Int. Cl.
  C07D 401/06 (2006.01)
  A61K 31/454 (2006.01)
  A61K 31/451 (2006.01)
(52) U.S. Cl. ............... 546/208; 546/226; 514/326; 514/330
(58) Field of Classification Search ............. 514/330, 514/326; 546/208, 226
  See application file for complete search history.

(56) References Cited

U.S. PATENT DOCUMENTS

| 5,576,290 A | 11/1996 | Hadley |
| 6,051,555 A | 4/2000 | Hadley |
| 6,166,037 A | 12/2000 | Budhu et al. |
| 6,350,760 B1 | 2/2002 | Bakshi et al. |
| 6,500,844 B1 | 12/2002 | Finke et al. |
| 6,511,994 B2 | 1/2003 | Kim et al. |

FOREIGN PATENT DOCUMENTS

| WO | WO 99/64002 | 12/1999 |
| WO | WO 00/76512 | 12/2000 |
| WO | WO 01/58891 | 8/2001 |
| WO | WO 01/70337 | 9/2001 |
| WO | WO 01/70708 | 9/2001 |
| WO | WO 00/74679 | 12/2001 |
| WO | WO 01/91752 | 12/2001 |
| WO | WO 02/068387 | 9/2002 |
| WO | WO 02/068388 | 9/2002 |

OTHER PUBLICATIONS

Poitout et. al. "Identification of a novel series of benzimidazoles as potent and selective antagonists of the human melanocortin-4 receptor" Bioorganic & Medicinal Chemistry Letters 2007, 17, 4464-4470.*
Guo et. al. "Synthesis and SAR of potent and orally bioavailable tert-butylpyrrolidine archetype derived melanocortin subtype-4 receptor modulators" Bioorganic & Medicinal Chemistry Letters 2008, 18, 3242-3247.*
Sebhat et. al. "Melanocortin subtype 4 receptor agonists: Structure—activity relationships about the 4-alkyl piperidine core" Bioorganic & Medicinal Chemistry Letters 2007, 17, 5720-5723.*
Hogan et. al. "Mapping the Binding Site of Melanocortin 4 Receptor Agonists: A Hydrophobic Pocket Formed by I3.28(125), I3.32(129), and I7.42(291) Is Critical for Receptor Activation" Journal of Medicinal Chemistry 2006, 49, 911-922.*
Fischer et. al. "Privileged structure based ligands for melanocortin receptors—Substituted benzylic piperazine derivatives" Bioorganic & Medicinal Chemistry Letters 2005, 15, 4973-4978.*
Wessells et al., J. of Urology, vol. 160(2), (1998), pp. 389-393, "Synthetic melanotropic peptide initiates erections in men with pyschogenic erectile dysfunction . . . ".
Giraudo et al., Brain Research, vol. 809 (1998), pp. 302-306, "Feeding effects of hypothalamic injection of melanocortin 4 receptor ligands".
Carpino, Exp. Opin. Ther. Patents (2000), vol. 10(6), pp. 819-831, "Patent focus on new anti-obesity agents: Sep. 1999-Feb. 2000".
Chaki et al., Exp. Opin. Ther. Patents (2001), vol. 11(11), pp. 1677-1692, "Recent advances in feeding suppressing agents: Potential therapeutic strategy for the treatment of obesity".
Wessells et al., Urology (2000), vol. 56, pp. 641-646, "Effect of an alpha-melanocyte stimulating hormone analog on penile erection and sexual desire in men with organic erectile dysfunction".
Dorr et al., Life Sciences, vol. 58 (1996), pp. 1777-1784, "Evaluation of melanotan-II, a superpotent cyclic melanotropic peptide in a pilot phase-I clinical study".
Moreland et al., Life Sciences, vol. 62 (1998), pp. 309-318, "Sildenafil, a novel inhibitor of phosphodiesterase type 5 in human corpus cavernosum smooth muscle cells".
Gingell et al., Exp. Opin. Ther. Patents (1999), vol. 9(12), pp. 1689-1696, "Emerging pharamcological therapies for erectile dysfunction".

(Continued)

*Primary Examiner*—Rita J. Desai
*Assistant Examiner*—David K O'Dell
(74) *Attorney, Agent, or Firm*—Baerbel R. Brown; Catherine D. Fitch

(57) ABSTRACT

Certain novel 4-substituted N-acylated piperidine derivatives are agonists of the human melanocortin receptor(s) and, in particular, are selective agonists of the human melanocortin-4 receptor (MC-4R). They are therefore useful for the treatment, control, or prevention of diseases and disorders responsive to the activation of MC-4R, such as obesity, diabetes, sexual dysfunction, including erectile dysfunction and female sexual dysfunction.

6 Claims, No Drawings

OTHER PUBLICATIONS

Dinsmore et al., BMJ, vol. 318 (1999), pp. 387-390, "ABC of sexual health: Erectile dysfunction".

Chen et al., Cell, vol. 91 (1997), pp. 789-798, "Exocrine gland dysfunction in MC5-R-deficient mice: . . . ".

Kask et al., Biochem. & Biophys. Res. Comm., vol. 245 (1998), pp. 90-93, "Selective antagonist for the melanocortin 4 receptor (HS014) increases food intake in free-feeding rats".

Huszar et al., Cell, vol. 88 (1997), pp. 131-141, "Targeted disruption of the melanocortin-4 receptor results in obesity in mice".

Pertwee, Exp. Opin. Invest. Drugs, vol. 9(7), (2000), pp. 1553-1571, "Cannabinoid receptor ligands: Clinical and neuropharmacological considerations, relevant to future drug discovery and development".

Wieland et al., Exp. Opin. Invest. Drugs, vol. 9(6) (2000), pp. 1327-1346, "The role of NPY in metabolic homeostasis: Implications for obesity therapy".

Proietto et al., Exp. Opin. Invest. Drugs, vol. 9(6), (2000), pp. 1317-1326, "Novel anti-obesity drugs".

Fukuyama et al., Tetrahedron Lett. (1997), vol. 38, No. 33, pp. 5831-5834, "2,4-Dinitrobenzenesulfonamides: A simple and practical method for the preparation of a variety of secondary amines and diamines".

Imai et al., Database STN No. 108:150205, Chem. Pharm. Bull., vol. 35(7), (1987), pp. 2646-2655, "Highly regioselective synthesis of trisubstituted pyrrolidines by 1,3-cycloaddition".

Getting et al., Drug News Perspect, vol. 13(1), (2000), pp. 19-27, "MC3-R as a novel target for antiinflammatory therapy".

Tomlinson et al., Database STN No. 135:166844 (2001).

Yoram et al., Current Opinion in Urology, vol. 7 (1997), pp. 349-353, "Oral pharmacotherapy in erectile dysfunction".

Peptides: Frontiers of Peptide Science, Fifteenth American Peptide Symposium, Jun. 14-19, 1997 (Nashville, TN).

Heaton et al., Int'l J. of Impotence Research, vol. 9 (1997), pp. 115-121, "A therapeutic taxonomy of treatments for erectile dysfunction: An evolutionary imperative".

Graul, Drug News & Perspectives, vol. 9(9) (1996), pp. 572-575, "Latest findings on the diagnosis and treatment of erectile dysfunction".

Corcos et al., Society for Neuroscience, vol. 23 (1997), Abstract 267.9, "HP 228 is a potent agonist of melanocortin receptor 4, and significantly attenuates obesity and diabetes in Zucker fatty rats".

Ho et al., J. Org. Chem. (1995), vol. 60, pp. 2271-2273, "Lithium-initiated imide formation. A simple method for N-acylation of 2-oxazolidinones and bornane-2,10-sultam".

Rohr et al., Heterocycles (1996), vol. 43, pp. 2131-2138, "Synthesis of 2-or/and 6-methylated analogues of isoguvacine (1,2,3,6-tetrahydropyridine-4-carboxylic acid) a $GABA_A$ Agonist".

Trost et al., J. Am. Chem. Soc. (1979), vol. 101, p. 6429-6432, "New conjunctive reagents. 2-acetoxymethyl-3-allyltrimethylsilane for methylenecyclopentane . . . ".

Olofson et al., J. Org. Chem., vol. 49 (1984), pp. 2081-2082, "A new reagent for the selective, high-yield N-dealkylation of tertiary amines . . . ".

Tsubouchi et al., 140:357387 CAPLUS.

Landaris et al., Intellectual Property Update, vol. 4 (2004), "Reach through claims: Bust or Boon?"

Baker Botts, Attorneys Practice Profiles News & Events (2002).

\* cited by examiner

US 7,700,778 B2

ACYLATED PIPERIDINE DERIVATIVES AS MELANOCORTIN-4 RECEPTOR AGONISTS

CROSS-REFERENCE TO RELATED APPLICATIONS

This application is a divisional application of U.S. Ser. No. 10/468,517, filed Aug. 19, 2003 now U.S. Pat. No. 7,012,084, a U.S. National Phase application under 35 U.S.C. §371 of PCT Application Ser. No. PCT/US02/08002, filed Feb. 25, 2002, which claims priority under 35 U.S.C. §119 from U.S. Provisional Application No. 60/272,259, filed Feb. 28, 2001.

FIELD OF THE INVENTION

The present invention relates to acylated piperidine derivatives, their synthesis, and their use as melanocortin receptor (MC-R) agonists. More particularly, the compounds of the present invention are selective agonists of the melanocortin-4 receptor (MC-4R) and are thereby useful for the treatment of disorders responsive to the activation of MC-4R, such as obesity, diabetes, male sexual dysfunction, and female sexual dysfunction.

BACKGROUND OF THE INVENTION

Pro-opiomelanocortin (POMC) derived peptides are known to affect food intake. Several lines of evidence support the notion that the G-protein coupled receptors (GPCRs) of the melanocortin receptor (MC-R) family, several of which are expressed in the brain, are the targets of POMC derived peptides involved in the control of food intake and metabolism. A specific single MC-R that may be targeted for the control of obesity has not yet been identified, although evidence has been presented that MC-4R signalling is important in mediating feed behavior (S. Q. Giraudo et al., "Feeding effects of hypothalamic injection of melanocortin-4 receptor ligands,"*Brain Research,* 80: 302-306 (1998)).

Evidence for the involvement of MC-R's in obesity includes: i) the agouti ($A^{vy}$) mouse which ectopically expresses an antagonist of the MC-1R, MC-3R and -4R is obese, indicating that blocking the action of these three MC-R's can lead to hyperphagia and metabolic disorders; ii) MC-4R knockout mice (D. Huszar et al., *Cell,* 88: 131-141 (1997)) recapitulate the phenotype of the agouti mouse and these mice are obese; iii) the cyclic heptapeptide MT-II (a non-selective MC-1R, -3R, -4R, and -5R agonist) injected intracerebroventricularly (ICV) in rodents, reduces food intake in several animal feeding models (NPY, ob/ob, agouti, fasted) while ICV injected SHU-9119 (MC-3R and 4R antagonist; MC-1R and -5R agonist) reverses this effect and can induce hyperphagia; iv) chronic intraperitoneal treatment of Zucker fatty rats with an α-NDP-MSH derivative (HP228) has been reported to activate MC-1R, -3R, -4R, and -5R and to attenuate food intake and body weight gain over a 12-week period (I. Corcos et al., "HP228 is a potent agonist of melanocortin receptor-4 and significantly attenuates obesity and diabetes in Zucker fatty rats," Society for Neuroscience Abstracts, 23: 673 (1997)).

Five distinct MC-R's have thus far been identified, and these are expressed in different tissues. MC-1R was initially characterized by dominant gain of function mutations at the Extension locus, affecting coat color by controlling phaeomelanin to eumelanin conversion through control of tyrosinase. MC-1R is mainly expressed in melanocytes. MC-2R is expressed in the adrenal gland and represents the ACTH receptor. MC-3R is expressed in the brain, gut, and placenta and may be involved in the control of food intake and thermogenesis. MC-4R is uniquely expressed in the brain, and its inactivation was shown to cause obesity (A. Kask, et al., "Selective antagonist for the melanocortin-4 receptor (HS014) increases food intake in free-feeding rats,"*Biochem. Biophys. Res. Commun.,* 245: 90-93 (1998)). MC-5R is expressed in many tissues, including white fat, placenta and exocrine glands. A low level of expression is also observed in the brain. MC-5R knockout mice reveal reduced sebaceous gland lipid production (Chen et al., *Cell,* 91: 789-798 (1997)).

Erectile dysfunction denotes the medical condition of inability to achieve penile erection sufficient for successful sexual intercourse. The term "impotence" is oftentimes employed to describe this prevalent condition. Approximately 140 million men worldwide, and, according to a National Institutes of Health study, about 30 million American men suffer from impotency or erectile dysfunction. It has been estimated that the latter number could rise to 47 million men by the year 2000. Erectile dysfunction can arise from either organic or psychogenic causes, with about 20% of such cases being purely psychogenic in origin. Erectile dysfunction increases from 40% at age 40, to 67% at age 75, with over 75% occurring in men over the age of 50. In spite of the frequent occurrence of this condition, only a small number of patients have received treatment because existing treatment alternatives, such as injection therapies, penile prosthesis implantation, and vacuum pumps, have been uniformly disagreeable [for a discussion, see "ABC of sexual health—erectile dysfunction,"*Brit. Med. J.* 318: 387-390 (1999)]. Only more recently have more viable treatment modalities become available, in particular orally active agents, such as sildenafil citrate, marketed by Pfizer under the brand name of Viagra®. (See "Emerging pharmacological therapies for erectile dysfunction,"*Exp. Opin. Ther. Patents* 9: 1689-1696 (1999)). Sildenafil is a selective inhibitor of type V phosphodiesterase (PDE-V), a cyclic-GMP-specific phosphodiesterase isozyme [see R. B. Moreland et al, "Sildenafil: A Novel Inhibitor of Phosphodiesterase Type 5 in Human Corpus Cavernosum Smooth Muscle Cells,"*Life Sci.,* 62: 309-318 (1998)]. Prior to the introduction of Viagra on the market, less than 10% of patients suffering from erectile dysfunction received treatment. Sildenafil is also being evaluated in the clinic for the treatment of female sexual dysfunction.

The regulatory approval of Viagra® for the oral treatment of erectile dysfunction has invigorated efforts to discover even more effective methods to treat erectile dysfunction. Several additional selective PDE-V inhibitors are in clinical trials. UK-114542 is a sildenafil backup from Pfizer with supposedly improved properties. IC-351 (ICOS Corp.) is claimed to have greater selectivity for PDE-V over PDE-VI than sildenafil. Other PDE-V inhibitors include M-54033 and M-54018 from Mochida Pharmaceutical Co. and E-4010 from Eisai Co., Ltd.

Other pharmacological approaches to the treatment of erectile dysfunction have been described [see, e.g., "Latest Findings on the Diagnosis and Treatment of Erectile Dysfunction,"*Drug News & Perspectives,* 9: 572-575 (1996); "Oral Pharmacotherapy in Erectile Dysfunction,"*Current Opinion in Urology,* 7: 349-353 (1997)]. A product under clinical development by Zonagen is an oral formulation of the alpha-adrenoceptor antagonist phentolamine mesylate under the brand name of Vasomax®. Vasomax® is also being evaluated for the treatment of female sexual dysfunction.

Drugs to treat erectile dysfunction act either peripherally or centrally. They are also classified according to whether they "initiate" a sexual response or "facilitate" a sexual response to prior stimulation [for a discussion, see "A Therapeutic Taxonomy of Treatments for Erectile Dysfunction: An Evolutionary Imperative,"*Int. J. Impotence Res.*, 9: 115-121 (1997)]. While sildenafil and phentolamine act peripherally and are considered to be "enhancers" or "facilitators" of the sexual response to erotic stimulation, sildenafil appears to be efficacious in both mild organic and psychogenic erectile dysfunction. Sildenafil has an onset of action of 30-60 minutes after an oral dose with the effect lasting about 4 hours, whereas phentolamine requires 5-30 minutes for onset with a duration of 2 hours. Although sildenafil is effective in a majority of patients, it takes a relatively long time for the compound to show the desired effects. The faster-acting phentolamine appears to be less effective and to have a shorter duration of action than sildenafil. Oral sildenafil is effective in about 70% of men who take it, whereas an adequate response with phentolamine is observed in only 35-40% of patients. Both compounds require erotic stimulation for efficacy. Since sildenafil indirectly increases blood flow in the systemic circulation by enhancing the smooth muscle relaxation effects of nitric oxide, it is contraindicated for patients with unstable heart conditions or cardiovascular disease, in particular patients taking nitrates, such as nitroglycerin, to treat angina. Other adverse effects associated with the clinical use of sildenafil include headache, flushing, dyspepsia, and "abnormal vision," the latter the result of inhibition of the type VI phosphodiesterase isozyme (PDE-VI), a cyclic-GMP-specific phosphodiesterase that is concentrated in the retina. "Abnormal vision" is defined as a mild and transient "bluish" tinge to vision, but also an increased sensitivity to light or blurred vision.

Synthetic melanocortin receptor agonists (melanotropic peptides) have been found to initiate erections in men with psychogenic erectile dysfunction [See H. Wessells et al., "Synthetic Melanotropic Peptide Initiates Erections in Men With Psychogenic Erectile Dysfunction: Double-Blind Placebo Controlled Crossover Study,"*J. Urol.*, 160: 389-393 (1998); *Fifteenth American Peptide Symposium*, Jun. 14-19, 1997 (Nashville, Tenn.)]. Activation of melanocortin receptors of the brain appears to cause normal stimulation of sexual arousal. In the above study, the centrally acting α-melanocyte-stimulating hormone analog, melanotan-II (MT-II), exhibited a 75% response rate, similar to results obtained with apomorphine, when injected intramuscularly or subcutaneously to males with psychogenic erectile dysfunction. MT-II is a synthetic cyclic heptapeptide, Ac-Nle-c[Asp-His-DPhe-Arg-Trp-Lys]-NH$_2$, which contains the 4-10 melanocortin receptor binding region common to α-MSH and adrenocorticotropin, but with a lactam bridge. It is a non-selective MC-1R, -3R, -4R, and -5R agonist (Dorr et al., *Life Sciences*, Vol. 58, 1777-1784, 1996). MT-II (also referred to as PT-14) (Erectide®) is presently in clinical development by Palatin Technologies, Inc. and TheraTech, Inc. as a non-penile subcutaneous injection formulation. It is considered to be an "initiator" of the sexual response. The time to onset of erection with this drug is relatively short (10-20 minutes) with a duration of action approximately 2.5 hours. Adverse reactions observed with MT-II include nausea, flushing, loss of appetite, stretching, and yawning and may be the result of activation of MC-1R, MC-2R, MC-3R, and/or MC -5R. MT-II must be administered parenterally, such as by subcutaneous, intravenous, or intramuscular route, since it is not absorbed into the systemic circulation when given by the oral route.

MT-II's erectogenic properties apparently are not limited to cases of psychogenic erectile dysfunction in that men with a variety of organic risk factors developed penile erections upon subcutaneous injection of the compound; moreover, the level of sexual desire was significantly higher after MT-II administration than after placebo [see H. Wessells, "Effect of an Alpha-Melanocyte Stimulating Hormone Analog on Penile Erection and Sexual Desire in Men with Organic Erectile Dysfunction,"*Urology*, 56: 641-646 (2000)].

Compositions of melanotropic peptides and methods for the treatment of psychogenic erectile dysfunction are disclosed in U.S. Pat. No. 5,576,290, assigned to Competitive Technologies. Methods of stimulating sexual response in females using melanotropic peptides have been disclosed in U.S. Pat. No. 6,051,555.

Spiropiperidine and piperidine derivatives have been disclosed in WO 99/64002 (16 Dec. 1999); WO 00/74679 (14 Dec. 2000); WO 01/70708 (27 Sep. 2001); WO 01/70337 (27 Sep. 2001); and WO 01/91752 (6 Dec. 2001) as agonists of the melanocortin receptor(s) and particularly as selective agonists of the MC-4R receptor and thereby useful for the treatment of diseases and disorders, such as obesity, diabetes, and sexual dysfunction, including erectile dysfunction and female sexual dysfunction.

Because of the unresolved deficiencies of the various pharmacological agents discussed above, there is a continuing need in the medical arts for improved methods and compositions to treat individuals suffering from psychogenic sexual dysfunction and/or organic sexual dysfunction. Such methods should have wider applicability, enhanced convenience and ease of compliance, short onset of action, reasonably long duration of action, and minimal side effects with few contraindications, as compared to agents now available.

It is therefore an object of the present invention to provide acylated piperidine derivatives which are melanocortin receptor agonists and thereby useful to treat obesity, diabetes, male sexual dysfunction, and female sexual dysfunction.

It is another object of the present invention to provide acylated piperidine derivatives which are selective agonists of the melanocortin-4 (MC-4R) receptor.

It is another object of the present invention to provide pharmaceutical compositions comprising the melanocortin receptor agonists of the present invention with a pharmaceutically acceptable carrier.

It is another object of the present invention to provide methods for the treatment or prevention of disorders, diseases, or conditions responsive to the activation of the melanocortin-4 receptor in a mammal in need thereof by administering the compounds and pharmaceutical compositions of the present invention.

It is another object of the present invention to provide methods for the treatment or prevention of obesity, diabetes mellitus, male sexual dysfunction, and female sexual dysfunction by administering the compounds and pharmaceutical compositions of the present invention to a mammal in need thereof.

It is another object of the present invention to provide methods for the treatment of erectile dysfunction by administering the compounds and pharmaceutical compositions of the present invention to a mammal in need thereof.

These and other objects will become readily apparent from the detailed description that follows.

SUMMARY OF THE INVENTION

The present invention relates to novel 4-substituted N-acylated piperidines of structural formula I:

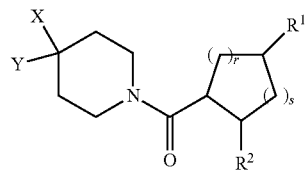

These piperidine derivatives are effective as melanocortin receptor agonists and are particularly effective as selective melanocortin-4 receptor (MC-4R) agonists. They are therefore useful for the treatment and/or prevention of disorders responsive to the activation of MC-4R, such as obesity, diabetes as well as male and female sexual dysfunction, in particular, male erectile dysfunction.

The present invention also relates to pharmaceutical compositions comprising the compounds of the present invention and a pharmaceutically acceptable carrier.

The present invention also relates to methods for the treatment or prevention of disorders, diseases, or conditions responsive to the activation of the melanocortin receptor in a mammal in need thereof by administering the compounds and pharmaceutical compositions of the present invention.

The present invention also relates to methods for the treatment or prevention of obesity, diabetes mellitus, male sexual dysfunction, and female sexual dysfunction by administering the compounds and pharmaceutical compositions of the present invention.

The present invention also relates to methods for treating erectile dysfunction by administering the compounds and pharmaceutical compositions of the present invention.

The present invention also relates to methods for treating erectile dysfunction by administering the compounds of the present invention in combination with a therapeutically effective amount of another agent known to be useful to treat or prevent the condition.

The present invention also relates to methods for treating or preventing obesity by administering the compounds of the present invention in combination with a therapeutically effective amount of another agent known to be useful to treat or prevent the condition.

DETAILED DESCRIPTION OF THE INVENTION

The present invention relates to 4-substituted N-acylated piperidine derivatives useful as melanocortin receptor agonists, in particular, as selective MC-4R agonists. Compounds of the present invention are described by structural formula I:

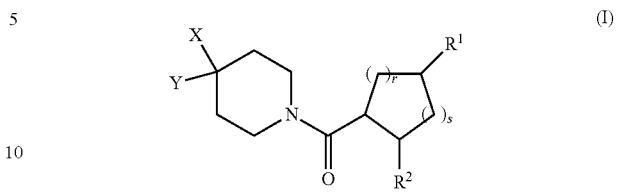

or a pharmaceutically acceptable salt thereof;
wherein
r is 1 or 2;
s is 0, 1, or 2;
n is 0, 1 or 2;
p is 0, 1, or 2;
$R^1$ is $NR^6R^7$ wherein $R^6$ and $R^7$ are independently selected from the group consisting of
  hydrogen,
  amidino,
  $C_{1-4}$ alkyliminoyl,
  $C_{1-10}$ alkyl,
  $(CH_2)_n$-$C_{3-7}$ cycloalkyl,
  $(CH_2)_n$-phenyl,
  $(CH_2)_n$-naphthyl, and
  $(CH_2)_n$-heteroaryl wherein heteroaryl is selected from the group consisting of
    (1) pyridinyl,
    (2) furyl,
    (3) thienyl,
    (4) pyrrolyl,
    (5) oxazolyl,
    (6) thiazolyl,
    (7) imidazolyl,
    (8) pyrazolyl,
    (9) isoxazolyl,
    (10) isothiazolyl,
    (11) pyrimidinyl,
    (12) pyrazinyl,
    (13) pyridazinyl,
    (14) quinolyl,
    (15) isoquinolyl,
    (16) benzimidazolyl,
    (17) benzofuryl,
    (18) benzothienyl,
    (19) indolyl,
    (20) benzthiazolyl, and
    (21) benzoxazolyl;

in which phenyl, naphthyl, and heteroaryl are unsubstituted or substituted with one to three groups independently selected from $R^3$; and $(CH_2)_n$, alkyl, and cycloalkyl are unsubstituted or substituted with one to three groups independently selected from $R^3$ and oxo; or $R^6$ and $R^7$ together with the nitrogen atom to which they are attached form a 4-8 membered mono- or bicyclic ring system optionally containing an additional heteroatom selected from O, S, and $NC_{1-4}$ alkyl;
$R^2$ is selected from the group consisting of
  phenyl,
  naphthyl, and
  heteroaryl wherein heteroaryl is selected from the group consisting of
    (1) pyridinyl,
    (2) furyl, (3) thienyl,
(4) pyrrolyl,
(5) oxazolyl,
(6) thiazolyl,
(7) imidazolyl,
(8) pyrazolyl,
(9) isoxazolyl,
(10) isothiazolyl,
(11) pyrimidinyl,
(12) pyrazinyl,
(13) pyridazinyl,
(14) quinolyl,
(15) isoquinolyl,
(16) benzimidazolyl,
(17) benzofuryl,
(18) benzothienyl,
(19) indolyl,
(20) benzthiazolyl, and
(21) benzoxazolyl;

in which phenyl, naphthyl, and heteroaryl are unsubstituted or substituted with one to three groups independently selected from $R^3$;

$R^3$ is selected from the group consisting of
  $C_{1-6}$ alkyl,
  $(CH_2)_n$-phenyl,
  $(CH_2)_n$-naphthyl,
  $(CH_2)_n$-heteroaryl,
  $(CH_2)_n C_{3-7}$ cycloalkyl,
  halogen,
  $OR^4$,
  $N(R^4)_2$,
  $C{\equiv}N$,
  $CO_2R^4$,
  $C(R^4)(R^4)N(R^4)_2$,
  $NO_2$,
  $(CH_2)_n NR^4 SO_2 R^4$,
  $(CH_2)_n SO_2 N(R^4)_2$,
  $(CH_2)_n S(O)_p R^4$,
  $(CH_2)_n NR^4 C(O)N(R^4)_2$,
  $(CH_2)_n C(O)N(R^4)_2$,
  $(CH_2)_n NR^4 C(O)R^4$,
  $(CH_2)_n NR^4 CO_2 R^4$,
  $CF_3$,
  $CH_2 CF_3$,
  $OCF_3$, and
  $OCH_2 CF_3$;

in which heteroaryl is as defined above and phenyl, naphthyl, and heteroaryl are unsubstituted or substituted with one to three substituents independently selected from halogen, $C_{1-4}$ alkyl, trifluoromethyl, and $C_{1-4}$ alkoxy; and $(CH_2)_n$ is unsubstituted or substituted with one to two groups independently selected from halogen and $C_{1-4}$ alkyl;

each $R^4$ is independently selected from the group consisting of
  hydrogen,
  $C_{1-6}$ alkyl,
  $(CH_2)_n$-phenyl,
  $(CH_2)_n$-naphthyl, and
  $(CH_2)_n C_{3-7}$ cycloalkyl;

two $R^4$ groups together with the atom to which they are attached form a 5- to 8-membered mono- or bi-cyclic ring system optionally containing an additional heteroatom selected from O, S, and $NC_{1-4}$ alkyl;

each $R^5$ is independently selected from the group consisting of
  hydrogen,
  $C_{1-8}$ alkyl,
  $(CH_2)_n$-phenyl,
  $(CH_2)_n$-naphthyl,
  $(CH_2)_n$-heteroaryl, and
  $(CH_2)_n C_{3-7}$ cycloalkyl;

wherein heteroaryl is as defined above; phenyl, naphthyl, and heteroaryl are unsubstituted or substituted with one to three groups independently selected from $R^3$; and alkyl, cycloalkyl, and $(CH_2)_n$ are unsubstituted or substituted with one to three groups independently selected from $R^3$ and oxo; or two $R^5$ groups together with the atom to which they are attached form a 5- to 8-membered mono- or bicyclic ring system optionally containing an additional heteroatom selected from O, S, and $NC_{1-4}$ alkyl;

X is selected from the group consisting of
  $C_{1-8}$ alkyl,
  $(CH_2)_n C_{3-8}$ cycloalkyl,
  $(CH_2)_n$-phenyl,
  $(CH_2)_n$-naphthyl,
  $(CH_2)_n$-heteroaryl,
  $(CH_2)_n$heterocyclyl,
  $(CH_2)_n C{\equiv}N$,
  $(CH_2)_n CON(R^5 R^5)$,
  $(CH_2)_n CO_2 R^5$,
  $(CH_2)_n COR^5$,
  $(CH_2)_n NR^5 C(O)R^5$,
  $(CH_2)_n NR^5 CO_2 R^5$,
  $(CH_2)_n NR^5 C(O)N(R^5)_2$,
  $(CH_2)_n NR^5 SO_2 R^5$,
  $(CH_2)_n S(O)_p R^5$,
  $(CH_2)_n SO_2 N(R^5)(R^5)$,
  $(CH_2)_n OR^5$,
  $(CH_2)_n OC(O)R^5$,
  $(CH_2)_n OC(O)OR^5$,
  $(CH_2)_n OC(O)N(R^5)_2$,
  $(CH_2)_n N(R^5)(R^5)$, and
  $(CH_2)_n NR^5 SO_2 N(R^5)(R^5)$;

wherein heteroaryl is as defined above, and phenyl, naphthyl, and heteroaryl are unsubstituted or substituted with one to three groups independently selected from $R^3$; and alkyl, $(CH_2)_n$, cycloalkyl, and heterocyclyl are unsubstituted or substituted with one to three groups independently selected from $R^3$ and oxo;

Y is selected from the group consisting of
  hydrogen,
  $C_{1-8}$ alkyl,
  $C_{2-6}$ alkenyl,
  $(CH_2)_n C_{3-8}$ cycloalkyl,
  $(CH_2)_n$-phenyl,
  $(CH_2)_n$-naphthy,
  $(CH_2)_n$-heteroaryl, and
  $(CH_2)_n$-heterocyclyl;

wherein heteroaryl is as defined above, and phenyl, naphthyl, and heteroaryl are unsubstituted or substituted with one to three groups independently selected from $R^3$; and alkyl, $(CH_2)_n$, cycloalkyl, and heterocyclyl are optionally substituted with one to three groups independently selected from $R^3$ and oxo.

In one embodiment of the compounds of structural formula I, $R^1$ is selected from the group consisting of hydrogen, $C_{1-6}$ alkyl, $(CH_2)_{0-1} C_{3-7}$ cycloalkyl, and $(CH_2)_{0-1}$-phenyl; wherein phenyl is unsubstituted or substituted with one to three groups independently selected from $R^3$; and alkyl and cycloalkyl are optionally substituted with one to three groups independently selected from $R^3$ and oxo.

In a second embodiment of the compounds of structural formula I, $R^2$ is phenyl or thienyl optionally substituted with one to three groups independently selected from $R^3$; in a class of this embodiment, $R^2$ is phenyl optionally substituted with one to three groups independently selected from $R^3$.

In a third embodiment of the compounds of structural formula I, X is selected from the group consisting of $C_{1-6}$ alkyl, $(CH_2)_n$-phenyl, $(CH_2)_n$-naphthyl, $(CH_2)_n$-heteroaryl, $(CH_2)_n$-heterocyclyl, $(CH_2)_nC(O)N(R^5)(R^5)$, $(CH_2)_nCO_2R^5$, $(CH_2)_nS(O)_pR^5$, $(CH_2)_nOR^5$, $(CH_2)_nNR^5C(O)R^5$, and $(CH_2)_n NR^5SO_2R^5$; wherein heteroaryl is as defined above, and phenyl, naphthyl, and heteroaryl are optionally substituted with one to three groups independently selected from $R^3$; alkyl and heterocyclyl are optionally substituted with one to three groups independently selected from $R^3$ and oxo; and the $(CH_2)_n$ group is optionally substituted with one to three groups independently selected from $R^4$, halogen, $S(O)_pR^4$, $N(R^4)_2$, and $OR^4$. In a class of this embodiment, X is selected from the group consisting of $C_{1-6}$ alkyl, $(CH_2)_{0-1}$-phenyl, $(CH_2)_{0-1}$-heteroaryl, $(CH_2)_{0-1}$-heterocyclyl, $(CH_2)_{0-1}NHC(O)R^5$, $(CH_2)_{0-1}CO_2R^5$, and $(CH_2)_{0-1}C(O)N(R^5)(R^5)$; wherein phenyl and heteroaryl are optionally substituted with one to three groups independently selected from $R^3$; and alkyl and heterocyclyl are optionally substituted with one to three groups independently selected from $R^3$ and oxo. In a subclass of this class, heteroaryl is selected from the group consisting of pyridyl, pyrazinyl, pyrimidinyl, triazolyl, tetrazolyl, thiadiazolyl, oxadiazolyl, pyrazolyl, and imidazolyl.

In a fourth embodiment of compounds of formula I, Y is selected from the group consisting of hydrogen, $C_{1-8}$ alkyl, $C_{2-6}$ alkenyl, $(CH_2)_nC_{5-7}$ cycloalkyl, $(CH_2)_n$-phenyl, $(CH_2)_n$-naphthyl, $(CH_2)_n$-heterocyclyl, and $(CH_2)_n$-heteroaryl, wherein phenyl, naphthyl, and heteroaryl are optionally substituted with one to three groups independently selected from $R^3$; and $(CH_2)_n$, alkyl, cycloalkyl, and heterocyclyl are optionally substituted with one to three groups independently selected from $R^3$ and oxo. In a class of this embodiment, Y is selected from the group consisting of hydrogen, $C_{1-8}$ alkyl, $C_{2-6}$ alkenyl, $C_{5-7}$ cycloalkyl, and phenyl; wherein phenyl is unsubstituted or substituted with one to three groups independently selected from $R^3$; and alkyl and cycloalkyl are unsubstituted or substituted with one to three groups independently selected from $R^3$ and oxo. In a subclass of this class, Y is cyclohexyl or $C_{1-6}$ alkyl; wherein the cyclohexyl and alkyl groups are unsubstituted or substituted with one to three groups independently selected from $R^3$ and oxo.

In a fifth embodiment of compounds of formula I, Y is hydrogen.

In yet a further embodiment of compounds of structural formula I, r is 1 or 2 and s is 1.

In yet a further embodiment of the compounds of the present invention, there are provided compounds of structural formula IIa or IIb of the indicated relative stereochemical configurations having the trans orientation of the $R^2$ and piperidinecarbonyl substituents:

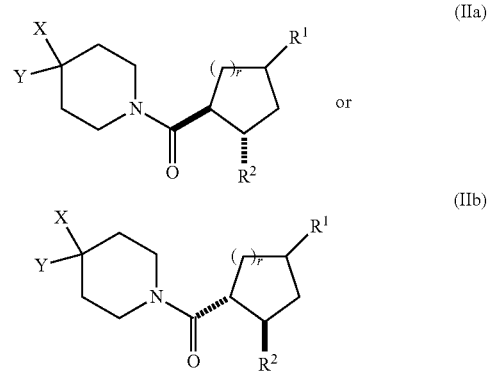

or a pharmaceutically acceptable salt thereof;
wherein
r is 1 or 2;
n is 0, 1, or 2;
p is 0, 1, or 2;
$R^1$ is $NR^6R^7$ wherein $R^6$ and $R^7$ are each independently selected from the group consisting of hydrogen, $C_{1-6}$ alkyl, $C_{3-6}$ cycloalkyl, $(CH_2)_{0-1}$ phenyl, $(CH_2)_{0-1}$ heteroaryl; wherein phenyl and heteroaryl are unsubstituted or substituted with one to three groups independently selected from $R^3$, and alkyl and cycloalkyl are unsubstituted or substituted with one to three groups independently selected from $R^3$ and oxo;
$R^2$ is phenyl or thienyl optionally substituted with one to three groups independently selected from $R^3$;
$R^3$ is selected from the group consisting of
  $C_{1-6}$ alkyl,
  $(CH_2)_n$-phenyl,
  $(CH_2)_n$-naphthyl,
  $(CH_2)_n$-heteroaryl,
  $(CH_2)_nC_{3-7}$ cycloalkyl,
  halogen,
  $OR^4$,
  $N(R^4)_2$,
  $C\equiv N$,
  $CO_2R^4$,
  $C(R^4)(R^4)N(R^4)_2$,
  $NO_2$,
  $(CH_2)_nNR^4SO_2R^4$,
  $(CH_2)_nS(O)_2N(R^4)_2$,
  $(CH_2)_nS(O)_pR^4$,
  $(CH_2)_nNR^4C(O)N(R^4)_2$,
  $(CH_2)_nC(O)N(R^4)_2$,
  $(CH_2)_nNR^4C(O)R^4$,
  $(CH_2)_nNR^4CO_2R^4$,
  $CF_3$,
  $CH_2CF_3$,
  $OCF_3$, and
  $OCH_2CF_3$;

in which heteroaryl is as defined above; phenyl, naphthyl, and heteroaryl are unsubstituted or substituted with one to two substituents independently selected from halogen, $C_{1-4}$ alkyl, trifluoromethyl, and $C_{1-4}$ alkoxy; and $(CH_2)_n$ is unsubstituted or substituted with one to two groups independently selected from halogen and $C_{1-4}$ alkyl;

each $R^4$ is independently selected from the group consisting of
hydrogen,
$C_{1-8}$ alkyl, and
$C_{3-6}$ cycloalkyl;

or two $R^4$ groups together with the atom to which they are attached form a 5- to 8-membered mono- or bicyclic ring system optionally containing an additional heteroatom selected from O, S, and $NC_{1-4}$ alkyl;

each $R^5$ is independently selected from the group consisting of
hydrogen,
$C_{1-5}$ alkyl,
phenyl,
naphthyl,
heteroaryl, and
$C_{5-6}$ cycloalkyl;

wherein heteroaryl is as defined above; phenyl, naphthyl, and heteroaryl are unsubstituted or substituted with one to three groups independently selected from $R^3$; and alkyl and cycloalkyl are unsubstituted or substituted with one to three groups independently selected from $R^3$ and oxo; or two $R^5$ groups together with the atom to which they are attached form a 5- to 8-membered mono- or bicyclic ring optionally containing an additional heteroatom selected from O, S, and $NR^4$;

Y is selected from the group consisting of
hydrogen,
$C_{1-8}$ alkyl,
$C_{2-6}$ alkenyl,
$(CH_2)_{0-1}C_{5-7}$ cycloalkyl,
$(CH_2)_{0-1}$-phenyl,
$(CH_2)_{0-1}$-naphthyl, and
$(CH_2)_{0-1}$-heteroaryl;

wherein phenyl, naphthyl, and heteroaryl are unsubstituted or substituted with one to three groups independently selected from $R^3$; and alkyl, $(CH_2)$, and cycloalkyl are unsubstituted or substituted with one to three groups independently selected from $R^3$ and oxo; and X is selected from the group consisting of:

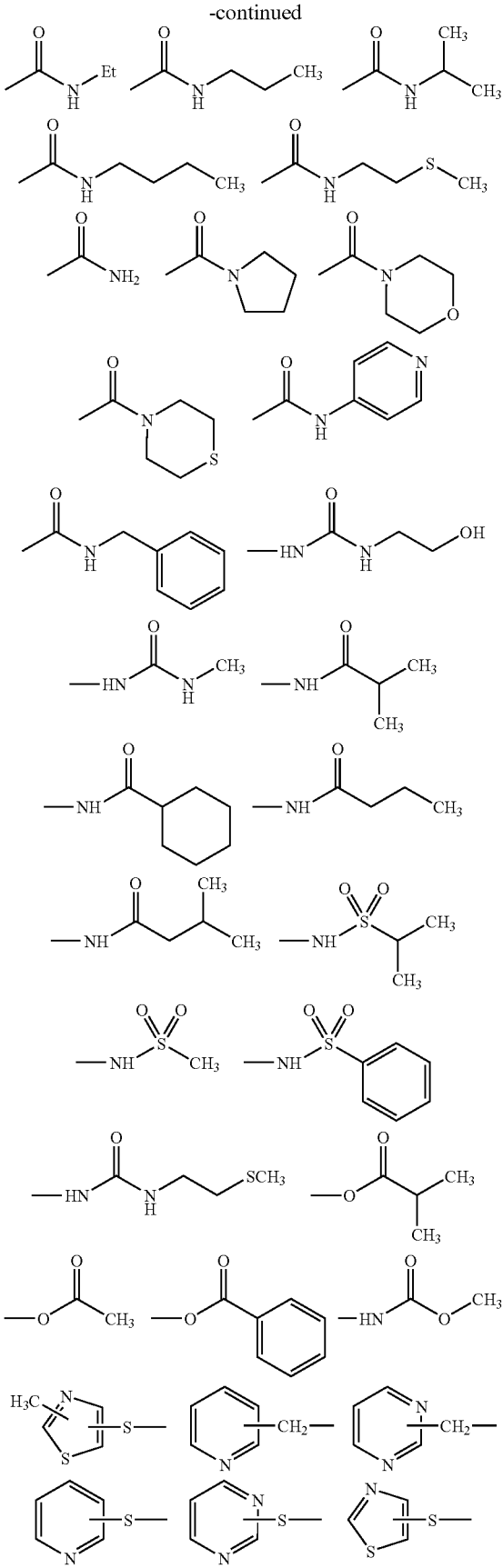

-continued

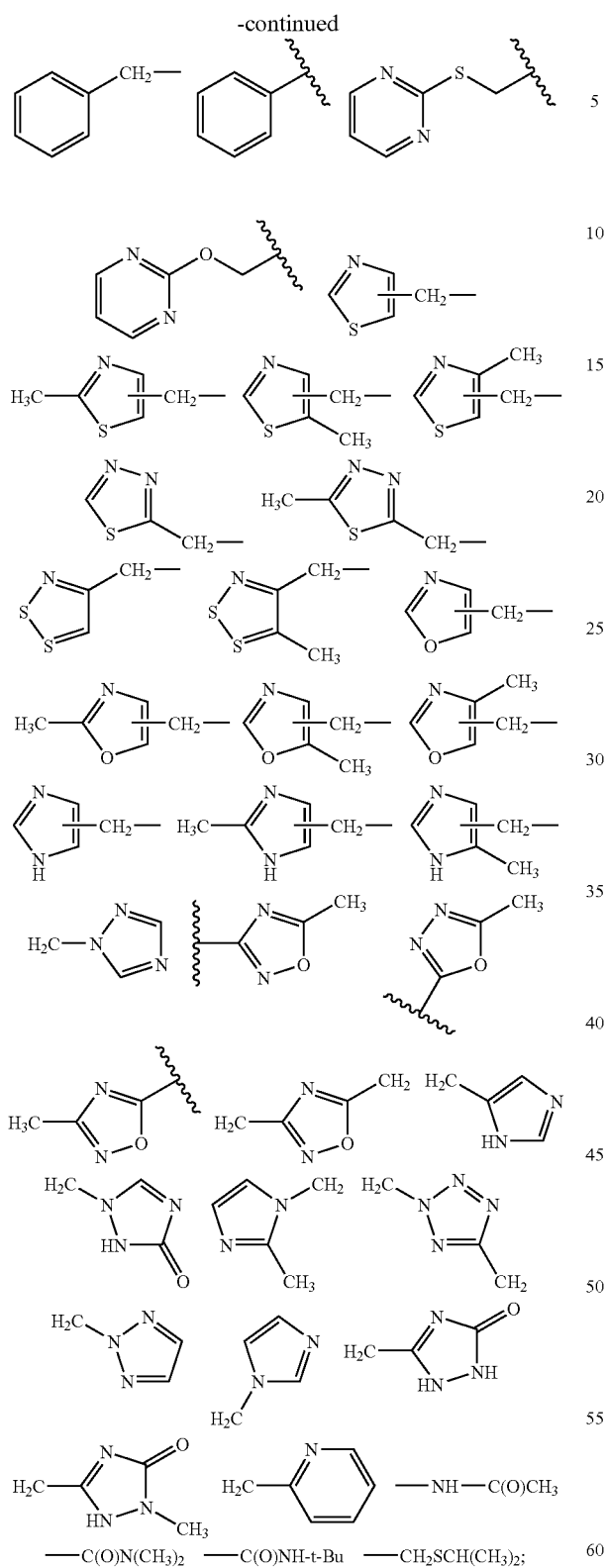

—C(O)N(CH₃)₂   —C(O)NH-t-Bu   —CH₂SCH(CH₃)₂;
—CH₂S(O)CH(CH₃)₂;   —CH₂S(O)₂CH(CH₃)₂;
—C(O)NHCH₂CH₂N(CH₃)₂;   C(O)CH(CH₃)₂;
—CH₂NHCOtBu;   —CH₂N(CH₃)COtBu;
—CH₂N(iPr)COMe;   —CH₂N(iPr)SO₂Me;

-continued
C(O)NHC(Me)₂CH₂OMe;   C(O)NHC(Me)₂CH₂OH;

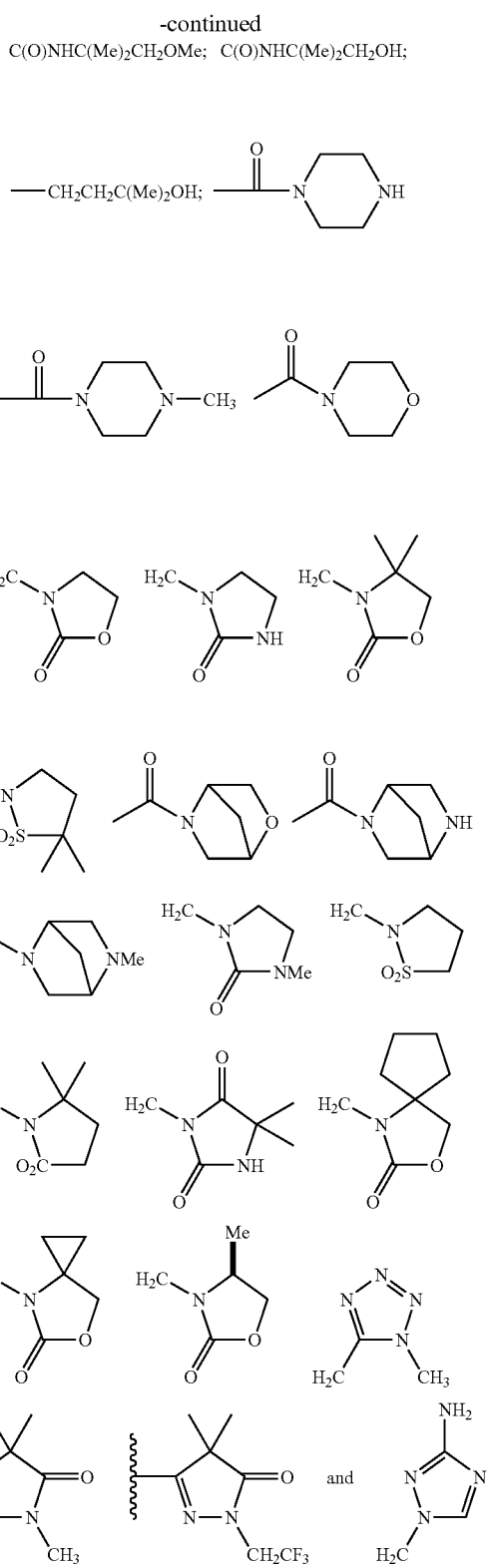

In yet a further embodiment of the compounds of the present invention, there are provided compounds of structural formula IIIa or IIIb of the indicated relative stereochemical configurations having the trans orientation of the phenyl and piperidinecarbonyl substituents:

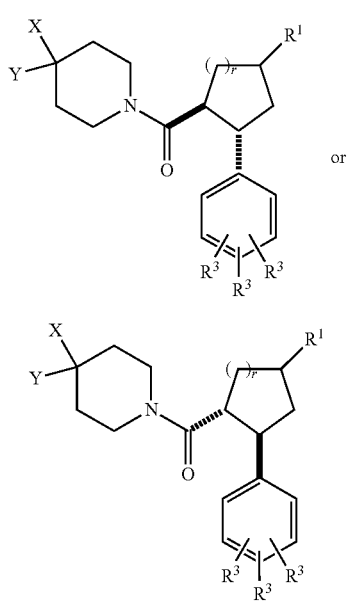

(IIIa)

or (IIIb)

or a pharmaceutically acceptable salt thereof;

wherein r is 1 or 2;

$R^1$ is $NR^6R^7$ wherein $R^6$ and $R^7$ are each independently hydrogen, $C_{1-4}$ alkyl, $(CH_2)_{0-1}C_{3-6}$ cycloalkyl, or $(CH_2)_{0-1}$ phenyl; in which phenyl is unsubstituted or substituted with one to three groups independently selected from $R^3$; and alkyl and cycloalkyl are unsubstituted or substituted with one to three groups independently selected from $R^3$ and oxo;

each $R^3$ is independently selected from the group consisting of hydrogen, halo, $C_{1-4}$ alkyl, trifluoromethyl, and $C_{1-4}$ alkoxy;

Y is cyclohexyl or phenyl; and

X is selected from the group consisting of

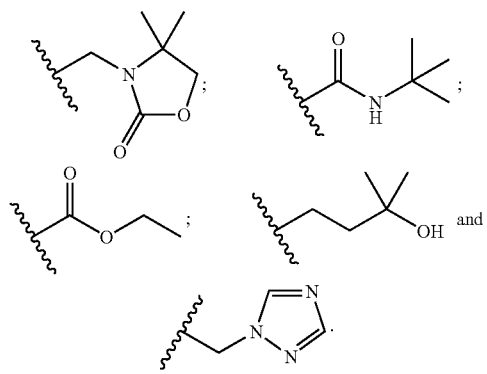

In yet a further embodiment of the compounds of the present invention, there are provided compounds of structural formula IVa or IVb of the indicated relative stereochemical configurations having the trans orientation of the phenyl and piperidinecarbonyl substituents:

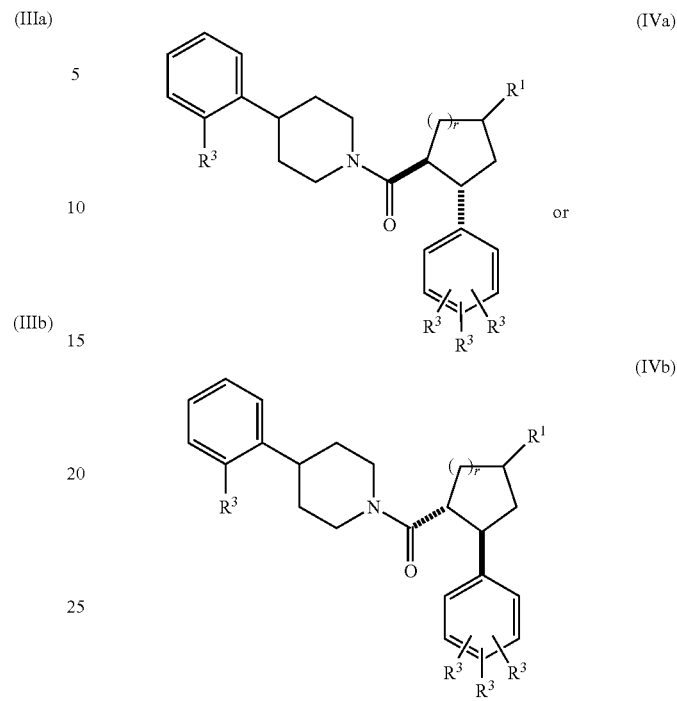

(IVa)

or (IVb)

or a pharmaceutically acceptable salt thereof;

wherein r is 1 or 2;

$R^1$ is $NR^6R^7$ wherein $R^6$ and $R^7$ are each independently hydrogen or $C_{1-4}$ alkyl; and $R^3$ is selected from the group consisting of
  $C_{1-6}$ alkyl,
  $(CH_2)_n$-phenyl,
  $(CH_2)_n$-naphthyl,
  $(CH_2)_n$-heteroaryl,
  $(CH_2)_nC_{3-7}$ cycloalkyl,
  halogen,
  $OR^4$,
  $N(R^4)_2$,
  $C\equiv N$,
  $CO_2R^4$,
  $C(R^4)(R^4)N(R^4)_2$,
  $NO_2$,
  $(CH_2)_nNR^4SO_2R^4$,
  $(CH_2)_nSO_2N(R^4)_2$,
  $(CH_2)_nS(O)_pR^4$,
  $(CH_2)_nNR^4C(O)N(R^4)_2$,
  $(CH_2)_nC(O)N(R^4)_2$,
  $(CH_2)_nNR^4C(O)R^4$,
  $(CH_2)_nNR^4CO_2R^4$,
  $CF_3$,
  $CH_2CF_3$,
  $OCF_3$, and
  $OCH_2CF_3$;

in which heteroaryl is as defined above; phenyl, naphthyl, and heteroaryl are unsubstituted or substituted with one to three substituents independently selected from halogen, $C_{1-4}$ alkyl, trifluoromethyl, and $C_{1-4}$ alkoxy; and $(CH_2)_n$ is unsubstituted or substituted with one to two groups independently selected from halogen and $C_{1-4}$ alkyl; and each $R^4$ is independently selected from the group consisting of
hydrogen,
$C_{1-6}$ alkyl,
$(CH_2)_n$-phenyl,
$(CH_2)_n$-naphthyl, and
$(CH_2)_n C_{3-7}$ cycloalkyl;

or two $R^4$ groups together with the atom to which they are attached form a 5- to 8-membered mono- or bicyclic ring system optionally containing an additional heteroatom selected from O, S, and $NC_{1-4}$ alkyl.

Illustrative but nonlimiting examples of compounds of the present invention that are useful as melanocortin agonists are the following:

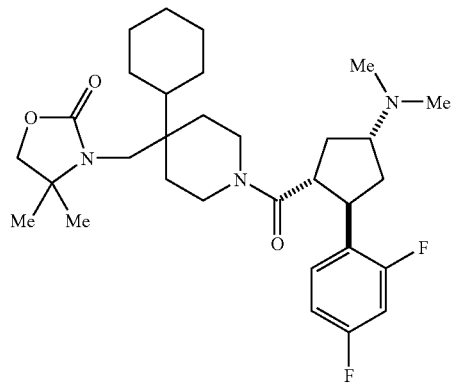

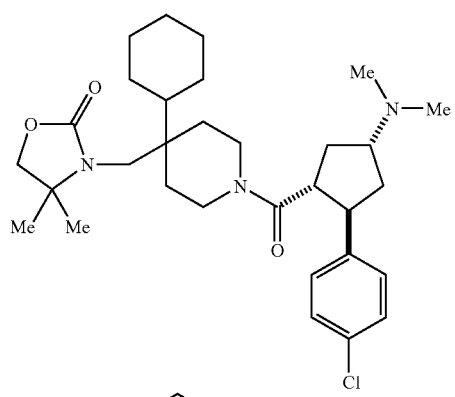

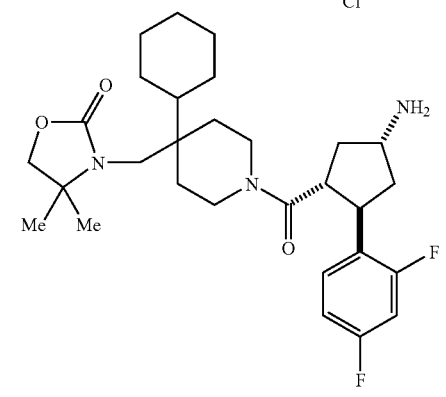

-continued

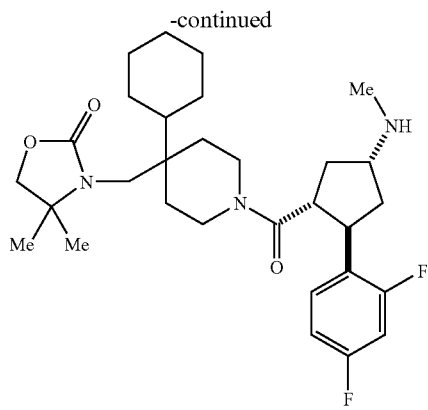

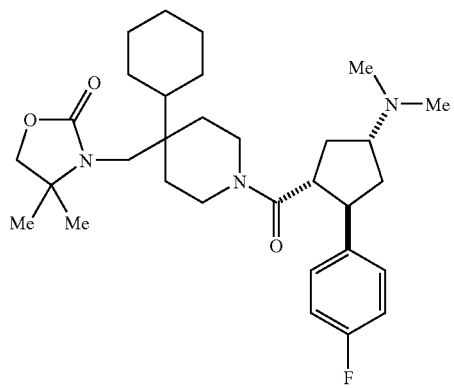

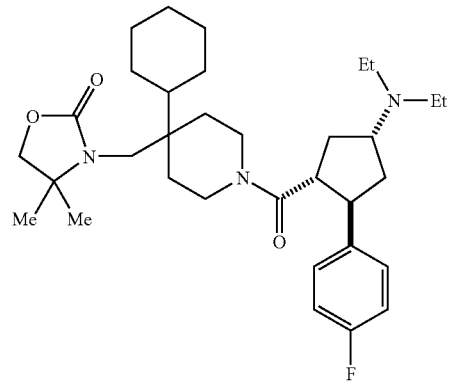

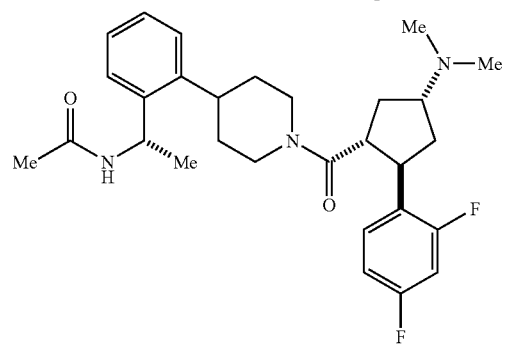

-continued

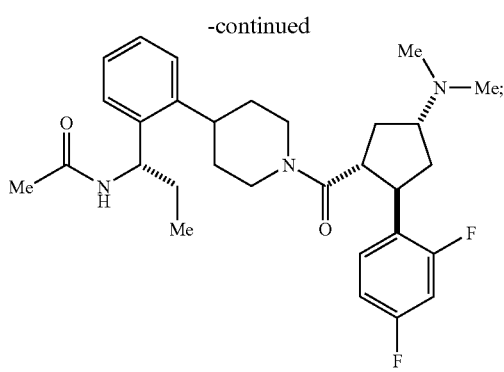

or a pharmaceutically acceptable salt thereof.

The compounds of structural formula I are effective as melanocortin receptor agonists and are particularly effective as selective agonists of MC-4R. They are therefore useful for the treatment and/or prevention of disorders responsive to the activation of MC-4R, such as obesity, diabetes as well as male and/or female sexual dysfunction, in particular, erectile dysfunction, and further in particular, male erectile dysfunction.

Another aspect of the present invention provides a method for the treatment or prevention of obesity or diabetes in a mammal in need thereof which comprises administering to said mammal a therapeutically or prophylactically effective amount of a compound of structural formula I.

Another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I.

Another aspect of the present invention provides a pharmaceutical composition comprising a compound of structural formula I and a pharmaceutically acceptable carrier.

Yet another aspect of the present invention provides a method for the treatment or prevention of male or female sexual dysfunction including erectile dysfunction which comprises administering to a mammal in need of such treatment or prevention a therapeutically or prophylactically effective amount of a compound of structural formula I in combination with a therapeutically effective amount of another agent known to be useful for the treatment of these conditions.

Throughout the instant application, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The term "halogen" is intended to include the halogen atoms fluorine, chlorine, bromine and iodine.

The term "$C_{1-4}$ alkyliminoyl" means $C_{1-3}C(=NH)$—.

The term "aryl" includes phenyl and naphthyl.

The term "heteroaryl" includes mono- and bicyclic aromatic rings containing from 1 to 4 heteroatoms selected from nitrogen, oxygen and sulfur. "5- or 6-membered heteroaryl" represents a monocyclic heteroaromatic ring, examples of which include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

The term "5- or 6-membered carbocyclyl" is intended to include non-aromatic rings containing only carbon atoms such as cyclopentyl and cyclohexyl.

The term "5 and 6-membered heterocyclyl" is intended to include non-aromatic heterocycles containing one to four heteroatoms selected from nitrogen, oxygen and sulfur. Examples of a 5 or 6-membered heterocyclyl include piperidine, morpholine, thiamorpholine, pyrrolidine, imidazolidine, tetrahydrofuran, piperazine, and the like.

Certain of the above defined terms may occur more than once in the above formula and upon such occurrence each term shall be defined independently of the other; thus for example, $NR^4R^4$ may represent $NH_2$, $NHCH_3$, $N(CH_3)CH_2CH_3$, and the like.

An embodiment of the term "mammal in need thereof" is a "human in need thereof," said human being either male or female.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction is often associated with age and is generally caused by a physical disease or as a side-effect of drug treatment.

By a melanocortin receptor "agonist" is meant an endogenous or drug substance or compound that can interact with a melanocortin receptor and initiate a pharmacological response characteristic of the melanocortin receptor. By a melanocortin receptor "antagonist" is meant a drug or a compound that opposes the melanocortin receptor-associated responses normally induced by another bioactive agent. The "agonistic" properties of the compounds of the present invention were measured in the functional assay described below. The functional assay discriminates a melanocortin receptor agonist from a melanocortin receptor antagonist.

By "binding affinity" is meant the ability of a compound/drug to bind to its biological target, in the present instance, the ability of a compound of structural formula I to bind to a melanocortin receptor. Binding affinities for the compounds of the present invention were measured in the binding assay described below and are expressed as $IC_{50}$'s.

"Efficacy" describes the relative intensity with which agonists vary in the response they produce even when they occupy the same number of receptors and with the same affinity. Efficacy is the property that enables drugs to produce responses. Properties of compounds/drugs can be categorized into two groups, those which cause them to associate with the receptors (binding affinity) and those that produce a stimulus (efficacy). The term "efficacy" is used to characterize the level of maximal responses induced by agonists. Not all agonists of a receptor are capable of inducing identical levels of maximal responses. Maximal response depends on the efficiency of receptor coupling, that is, from the cascade of events, which, from the binding of the drug to the receptor, leads to the desired biological effect.

The functional activities expressed as $EC_{50}$'s and the "agonist efficacy" for the compounds of the present invention at a particular concentration were measured in the functional assay described below.

Optical Isomers—Diastereomers—Geometric Isomers—Tautomers

Compounds of structural formula I contain one or more asymmetric centers and can thus occur as racemates and racemic mixtures, single enantiomers, diastereomeric mixtures and individual diastereomers. The present invention is meant to comprehend all such isomeric forms of the compounds of structural formula I.

Some of the compounds described herein contain olefinic double bonds, and unless specified otherwise, are meant to include both E and Z geometric isomers.

Some of the compounds described herein may exist as tautomers such as keto-enol tautomers. The individual tautomers as well as mixtures thereof are encompassed within the compounds of structural formula I.

Compounds of structural formula I may be separated into their individual diastereoisomers by, for example, fractional crystallization from a suitable solvent, for example methanol or ethyl acetate or a mixture thereof, or via chiral chromatography using an optically active stationary phase. Absolute stereochemistry may be determined by X-ray crystallography of crystalline products or crystalline intermediates which are derivatized, if necessary, with a reagent containing an asymmetric center of known absolute configuration.

Alternatively, any stereoisomer of a compound of the general formula I, IIa, IIb, IIIa, IIIb, IVa, and IVb may be obtained by stereospecific synthesis using optically pure starting materials or reagents of known absolute configuration.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Particularly preferred are citric, fumaric, hydrobromic, hydrochloric, maleic, phosphoric, sulfuric, and tartaric acids.

It will be understood that, as used herein, references to the compounds of Formula I are meant to also include the pharmaceutically acceptable salts.

Utility

Compounds of formula I are melanocortin receptor agonists and as such are useful in the treatment, control or prevention of diseases, disorders or conditions responsive to the activation of one or more of the melanocortin receptors including, but are not limited to, MC-1, MC-2, MC-3, MC-4, or MC-5. Such diseases, disorders or conditions include, but are not limited to, obesity (by reducing appetite, increasing metabolic rate, reducing fat intake or reducing carbohydrate craving), diabetes mellitus (by enhancing glucose tolerance, decreasing insulin resistance), hypertension, hyperlipidemia, osteoarthritis, cancer, gall bladder disease, sleep apnea, depression, anxiety, compulsion, neuroses, insomnia/sleep disorder, substance abuse, pain, male and female sexual dysfunction (including impotence, loss of libido and erectile dysfunction), fever, inflammation, immunemodulation, rheumatoid arthritis, skin tanning, acne and other skin disorders, neuroprotective and cognitive and memory enhancement including the treatment of Alzheimer's disease. Some compounds encompassed by formula I show highly selective affinity for the melanocortin-4 receptor relative to MC-1R, MC-2R, MC-3R, and MC-5R, which makes them especially useful in the prevention and treatment of obesity, as well as male and/or female sexual dysfunction, including erectile dysfunction.

"Male sexual dysfunction" includes impotence, loss of libido, and erectile dysfunction.

"Erectile dysfunction" is a disorder involving the failure of a male mammal to achieve erection, ejaculation, or both. Symptoms of erectile dysfunction include an inability to achieve or maintain an erection, ejaculatory failure, premature ejaculation, or inability to achieve an orgasm. An increase in erectile dysfunction and sexual dysfunction can have numerous underlying causes, including but not limited to (1) aging, (b) an underlying physical dysfunction, such as trauma, surgery, and peripheral vascular disease, and (3) side-effects resulting from drug treatment, depression, and other CNS disorders.

"Female sexual dysfunction" can be seen as resulting from multiple components including dysfunction in desire, sexual arousal, sexual receptivity, and orgasm related to disturbances in the clitoris, vagina, periurethral glans, and other trigger points of sexual function. In particular, anatomic and functional modification of such trigger points may diminish the orgasmic potential in breast cancer and gynecologic cancer patients. Treatment of female sexual dysfunction with an MC-4 receptor agonist can result in improved blood flow, improved lubrication, improved sensation, facilitation of reaching orgasm, reduction in the refractory period between orgasms, and improvements in arousal and desire. In a broader sense, "female sexual dysfunction" also incorporates sexual pain, premature labor, and dysmenorrhea.

Administration and Dose Ranges

Any suitable route of administration may be employed for providing a mammal, especially a human with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally or topically.

The effective dosage of active ingredient employed may vary depending on the particular compound employed, the mode of administration, the condition being treated and the severity of the condition being treated. Such dosage may be ascertained readily by a person skilled in the art.

When treating obesity, in conjunction with diabetes and/or hyperglycemia, or alone, generally satisfactory results are obtained when the compounds of the present invention are administered at a daily dosage of from about 0.001 milligram to about 100 milligrams per kilogram of animal body weight, preferably given in a single dose or in divided doses two to six times a day, or in sustained release form. In the case of a 70 kg adult human, the total daily dose will generally be from about 0.07 milligrams to about 3500 milligrams. This dosage regimen may be adjusted to provide the optimal therapeutic response.

When treating diabetes mellitus and/or hyperglycemia, as well as other diseases or disorders for which compounds of formula I are useful, generally satisfactory results are obtained when the compounds of the present invention are administered at a daily dosage of from about 0.001 milligram to about 100 milligram per kilogram of animal body weight, preferably given in a single dose or in divided doses two to six times a day, or in sustained release form. In the case of a 70 kg adult human, the total daily dose will generally be from about 0.07 milligrams to about 350 milligrams. This dosage regimen may be adjusted to provide the optimal therapeutic response.

For the treatment of sexual dysfunction compounds of the present invention are given in a dose range of 0.001 milligram to about 100 milligram per kilogram of body weight, preferably as a single dose orally or as a nasal spray.

Combination Therapy

Compounds of Formula I may be used in combination with other drugs that are used in the treatment/prevention/suppression or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I.

Examples of other active ingredients that may be combined with a compound of Formula I for the treatment or prevention of obesity and/or diabetes, either administered separately or in the same pharmaceutical compositions, include, but are not limited to:

(a) insulin sensitizers including (i) PPARγ agonists such as the glitazones (e.g. troglitazone, pioglitazone, englitazone, MCC-555, BRL49653 and the like), and compounds disclosed in WO97/27857, 97/28115, 97/28137 and 97/27847; (ii) biguanides such as metformin and phenformin;

(b) insulin or insulin mimetics;

(c) sulfonylureas, such as tolbutamide and glipizide;

(d) α-glucosidase inhibitors (such as acarbose), (e) cholesterol lowering agents such as (i) HMG-CoA reductase inhibitors (lovastatin, simvastatin, pravastatin, fluvastatin, atorvastatin, and other statins), (ii) sequestrants (cholestyramine, colestipol and a dialkylaminoalkyl derivatives of a cross-linked dextran), (ii) nicotinyl alcohol nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption for example beta-sitosterol and (acyl CoA:cholesterol acyltransferase) inhibitors for example melinamide, (v) probucol, (vi) vitamin E, and (vii) thyromimetics;

(f) PPARδ agonists, such as those disclosed in WO97/28149;

(g) anti-obesity serotonergic agents, such as fenfluramine, dexfenfluramine, phentermine, and sibutramine;

(h) β3-adrenoreceptor agonists;

(i) pancreatic lipase inhibitors, such as orlistat;

(j) feeding behavior modifying agents, such as neuropeptide Y Y1 and Y5 antagonists, such as those disclosed in WO 97/19682, WO 97/20820, WO 97/20821, WO 97/20822, WO 97/20823, WO 01/14376, and U.S. Pat. No. 6,191,160;

(k) orexin-1 receptor antagonists;

(l) PPARα agonists such as described in WO 97/36579 by Glaxo;

(m) PPARγ antagonists as described in WO97/10813;

(n) serotonin reuptake inhibitors such as fluoxetine, paroxetine, and sertraline;

(o) growth hormone secretagogues, such as MK-0677;

(p) cannabinoid receptor ligands, such as cannabinoid $CB_1$ receptor antagonists or inverse agonists; and (q) protein tyrosine phosphatase-1B (PTP-1B) inhibitors.

Examples of anti-obesity agents that can be employed in combination with a compound of Formula I are disclosed in "Patent focus on new anti-obesity agents," *Exp. Opin. Ther. Patents,* 10: 819-831 (2000); "Novel anti-obesity drugs," *Exp. Opin. Invest. Drugs,* 9: 1317-1326 (2000); and "Recent advances in feeding suppressing agents: potential therapeutic strategy for the treatment of obesity, *Exp. Pin. Ther. Patents,* 11: 1677-1692 (2001). The role of neuropeptide Y in obesity is discussed in *Exp. Opin. Invest. Drugs,* 9: 1327-1346 (2000). Cannabinoid receptor ligands are discussed in *Exp. Opin. Invest. Drugs,* 9: 1553-1571 (2000).

Examples of other active ingredients that may be combined with a compound of Formula I for the treatment or prevention of male or female sexual dysfunction, in particular, male erectile dysfunction, either administered separately or in the same pharmaceutical compositions, include, but are not limited to (a) type V cyclic-GMP-specific phosphodiesterase (PDE-V) inhibitors, including sildenafil and (6R, 12aR)-2,3,6,7,12,12a-hexahydro-2-methyl-6-(3,4-methylenedioxyphenyl)-pyrazino[2',1':6,1]pyrido[3,4b]indole-1,4-dione (IC-351); (b) alpha-adrenergic receptor antagonists, including phentolamine and yohimbine or pharmaceutically acceptable salts thereof; (c) dopamine receptor agonists, such as apomorphine or pharmaceutically acceptable salts thereof; and (d) nitric oxide (NO) donors.

Pharmaceutical Compositions

Another aspect of the present invention provides pharmaceutical compositions which comprises a compound of Formula I and a pharmaceutically acceptable carrier. The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystaline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Preparation of Compounds of the Invention

The compounds of Formula I of the present invention can be prepared according to the procedures of the following Schemes and Examples, using appropriate materials and are further exemplified by the following specific examples. Moreover, by utilizing the procedures described in detail in PCT International Application Publication No. WO 99/64002 (published 16 Dec. 1999) and WO 00/74679 (published 14 Dec. 2000), the contents of each of which are incorporated by reference herein in their entirety, in conjunction with the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those described previously hereinabove. The free amine bases corresponding to the isolated salts can be generated by neutralization with a suitable base, such as aqueous sodium hydrogencarbonate, sodium carbonate, sodium hydroxide, and potassium hydroxide, and extraction of the liberated amine free base into an organic solvent followed by evaporation. The amine free base isolated in this manner can be further converted into another pharmaceutically acceptable salt by dissolution in an organic solvent followed by addition of the appropriate acid and subsequent evaporation, precipitation, or crystallization. All temperatures are degrees Celsius unless otherwise noted. Mass spectra (MS) were measured by electron-spray ion-mass spectroscopy.

The phrase "standard peptide coupling reaction conditions" means coupling a carboxylic acid with an amine using an acid activating agent such as EDC, DCC, and BOP in an inert solvent such as dichloromethane in the presence of a catalyst such as HOBT. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., *Protective Groups in Organic Synthesis*, John Wiley & Sons, Inc., New York, N.Y., 1991. CBZ and BOC are commonly used protecting groups in organic synthesis, and their removal conditions are known to those skilled in the art. For example, CBZ may be removed by catalytic hydrogenation in the presence of a noble metal or its oxide such as palladium on activated carbon in a protic solvent such as methanol or ethanol. In cases where catalytic hydrogenation is contraindicated due to the presence of other potentially reactive functionalities, removal of CBZ groups can also be achieved by treatment with a solution of hydrogen bromide in acetic acid or by treatment with a mixture of TFA and dimethylsulfide. Removal of BOC protecting groups is carried out with a strong acid, such as trifluoroacetic acid, hydrochloric acid, or hydrogen chloride gas, in a solvent such as methylene chloride, methanol, or ethyl acetate.

Abbreviations Used in the Description of the Preparation of the Compounds of the Present Invention:

| | |
|---|---|
| BOC (boc) | t-butyloxycarbonyl |
| BOP | benzotriazol-1-yloxytris(dimethylamino)phosphonium hexafluorophosphate |
| Bu | butyl |
| calc. | calculated |
| CBZ (Cbz) | benzyloxycarbonyl |
| c-hex | cyclohexyl |
| c-pen | cyclopentyl |
| c-pro | cyclopropyl |
| DEAD | diethyl azodicarboxylate |
| DIEA | diisopropylethylamine |
| DMAP | 4-dimethylaminopyridine |
| DMF | N,N-dimethylformamide |
| EDC | 1-(3-dimethylaminopropyl)3-ethylcarbodiimide HCl |
| eq. | equivalent(s) |
| ES-MS | electron spray ion-mass spectroscopy |
| Et | ethyl |
| EtOAc | ethyl acetate |
| HATU | N-[(dimethylamino)-1H-1,2,3-triazolo[4,5-b]pyridin-1-ylmethylene]-N-methylmethanaminium hexafluorophosphate N-oxide |
| HOAt | 1-hydroxy-7-azabenzotriazole |
| HOBt | 1-hydroxybenzotriazole hydrate |
| HPLC | high performance liquid chromatography |
| LDA | lithium diisopropylamide |
| MC-xR | melanocortin receptor (x being a number) |
| Me | methyl |
| MF | molecular formula |
| MS | mass spectrum |
| Ms | methanesulfonyl |
| OTf | trifluoromethanesulfonyl |
| Ph | phenyl |
| Phe | phenylalanine |
| Pr | propyl |
| prep. | prepared |
| PyBrop | bromo-tris-pyrrolidino-phosphonium hexafluorophosphate |
| r.t. | room temperature |
| TFA | trifluoroacetic acid |
| THF | tetrahydrofuran |
| TLC | thin-layer chromatography. |

Reaction Schemes A-F illustrate the methods employed in the synthesis of the compounds of the present invention of structural formula I. All substituents are as defined above unless indicated otherwise.

The synthesis of the novel compounds of structural formula I which are the subject of this invention may be accomplished by one or more of several similar routes. In all cases it is necessary to effect an amide bond coupling between a substituted piperidine of general formula 1 and a cycloalkyl carboxylic acid derivative of general formula 2 as shown in reaction Schemes A-C below. Once the amide bond coupling reaction is accomplished, it may be necessary to further synthetically modify the coupled product to incorporate the desired substituents on the cycloalkyl carboxylic acid ring or to remove protecting groups. Reaction Scheme A illustrates the synthetic methodology in the most general case where a cycloalkyl carboxylic acid derivative 2 bearing the desired $R^1$ substituent is coupled with a substituted piperidine of general formula 1 to afford an amide corresponding to the title compounds of structural formula I. The amide bond coupling reaction illustrated in reaction Scheme A is conducted in an appropriate inert solvent such as methylene chloride, dimethylformamide, or the like and may be performed with a variety of reagents suitable for amide coupling reactions such as 1-(3-dimethylaminopropyl)-3-ethylcarbodiimide hydrochloride (EDC) or benzotriazol-1-yloxytripyrrolidinephosphonium hexafluorophosphate (PyBOP). Preferred conditions for the amide bond coupling reaction shown in reaction Scheme A are known to those skilled in organic synthesis. Such modifications may include, but are not limited to, the use of basic reagents such as triethylamine (TEA) or N-methylmorpholine (NMM), or the addition of an additive such as 1-hydroxybenzotriazole (HOBt). Alternatively, 4-substituted piperidines of formula 1 may be treated with an active ester or acid chloride derived from carboxylic acid 2 which also affords compounds of structural formula I. The amide bond coupling shown in reaction Scheme A is usually conducted at temperatures between 0° C. and room temperature, occasionally at elevated temperatures, and the coupling reaction is typically conducted for periods of 1 to 24 hours.

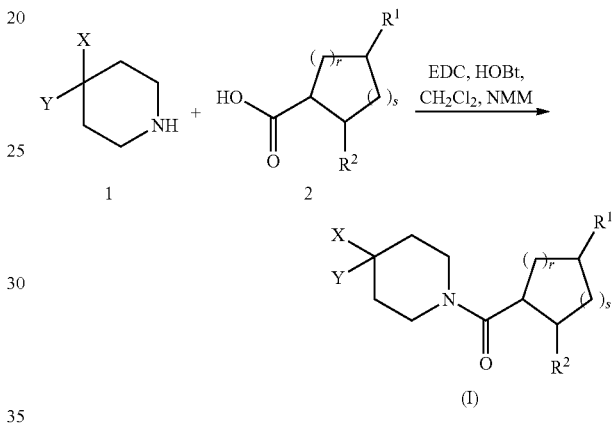

Scheme A

Reaction Schemes B and C illustrate the synthesis of the novel compounds of structural formula I when it is preferred to effect the amide bond coupling step prior to incorporation of the basic substituent $R^1$ as mentioned above. Reaction Scheme B illustrates a preferred method for the synthesis of compounds of structural formula I which employs a piperidine of general formula 1 and a cycloalkanone carboxylic acid of general formula 3 as the partners in the amide bond coupling step. The piperidine of formula 1 and the carboxylic acid of formula 3 are first coupled to afford an amide of general formula 4 using the reagents and conditions described for the generalized amide coupling shown in reaction Scheme A. The $R^1$ substituent ($R^1$=$NR^6R^7$) may then be incorporated at the position of the carbonyl group by performing a reductive amination reaction with an amine of general formula 5. Typical conditions for effecting such a reductive amination include preforming an imine 6 from ketone 3 and amine 5 followed by reduction of the intermediate imine with reducing agents such as sodium borohydride, sodium cyanoborohydride or sodium triacetoxyborohydride. Formation of the intermediate imine 6 derived from piperidine 1 and acid 3 may occur spontaneously in solution or it may be promoted with agents such as titanium(IV) isopropoxide in a solvent such as methanol or with anhydrous magnesium sulfate in chloroform. The formation of the imine 6 is generally performed at temperatures between 0° C. and the reflux temperature of the solvent being used, frequently at room temperature. The imine formation step is generally allowed to proceed to completion over a period of several hours to 1 day prior to the reduction step which minimizes the formation of secondary alcohols formed by simple reduction of the keto group in compounds of general formula 4. The intermediate imine 6 may in some cases be isolated and purified, however it is generally preferred to use it directly in the reduction step. The reduction of the imine 6 is typically conducted in an alcoholic solvent such as methanol or ethanol at temperatures between 0° C. and room temperature, and the reduction is generally completed in periods of several hours or less.

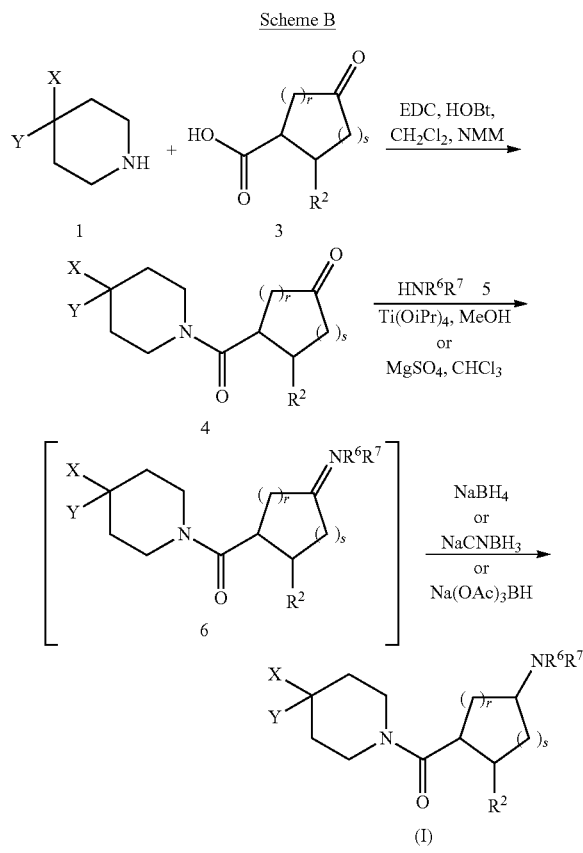

Reaction Scheme C illustrates a preferred method for the synthesis of compounds of structural formula I which employs a piperidine of general formula 1 and a hydroxyl-substituted cycloalkyl carboxylic acid of general formula 7 as the partners in the amide bond coupling step. The amide bond coupling step between piperidine 1 and carboxylic acid 7 is performed first, typically using a carbodiimide reagent like EDC to promote the coupling as described above. The hydroxyl-substituted amide 8 which is produced is then further synthetically modified to incorporate the $R^1$ substituent present in the title compounds of structural formula I. A variety of methods known to those skilled in organic synthesis may be used to incorporate the $R^1$ substituent. For instance, the hydroxyl group of compounds of general formula 8 may be oxidized using a variety of methods to afford carbonyl compounds of general formula 4. The resulting ketoamides of general formula 4 may then be converted to the title compounds of structural formula I using the reductive amination reaction described in reaction Scheme B.

Occasionally, it may be preferable to utilize hydroxyl-substituted compounds of general formula 8 in a Fukuyama-Mitsunobu reaction (Fukuyama, T.; Cheung, M.; Jow, C. -K.; Hidai, Y.; Kan, T. *Tetrahedron Lett.* 1997, 33, 5831-4) sequence as shown in reaction Scheme C. In this method for the synthesis of the novel title compounds of structural formula I, the intermediate hydroxyl-substituted cycloalkylamide 8 is reacted with a 2,4-dinitrobenzenesulfonamide of general formula 9 in the presence of triphenylphosphine and an azodicarboxylate reagent such as diethyl azodicarboxylate (DEAD). The reaction is performed in a suitable aprotic solvent such as benzene, toluene or tetrahydrofuran, typically at room temperature, and the reaction is generally complete in 0.5-3 hours. The product of this reaction is the secondary 2,4-dintrobenzenesulfonamide of general formula 10, which may then be readily converted to a title compound of structural formula I wherein $R^7$=H. The deprotection of the sulfonamide group is accomplished by reaction of 10 with either a base like n-propylamine in a solvent like methylene chloride or by reaction of 10 with a nucleophilic reagent such as mercaptoacetic acid with triethylamine in methylene chloride. In either case the reaction is typically conducted at room temperature, for periods of 5 minutes to one hour. An advantage of the Fukuyama-Mitsunobu reaction sequence is that the stereochemistry of the carbon atom undergoing substitution is cleanly inverted. Thus if the hydroxyl-substituted cycloalkylamide 8 is a single diastereoisomer, then the product 10 will be a single diastereoisomer also. This is in contrast to the reductive amination strategy discussed in reaction Scheme B which generally affords a mixture of epimeric products.

The secondary amine of formula I ($R^7$=H) shown in reaction Scheme C may then be further synthetically modified using a variety of methods known in organic synthesis to incorporate other embodiments of the $R^7$ substituent. For instance, compounds of structural formula I where $R^7$=H may be subjected to a reductive amination reaction with an appropriate aldehyde or ketone using the conditions described in reaction Scheme B.

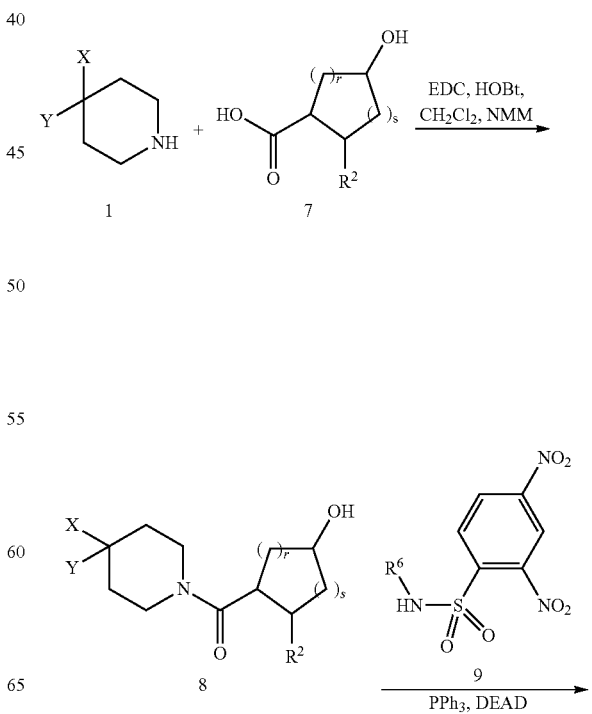

-continued

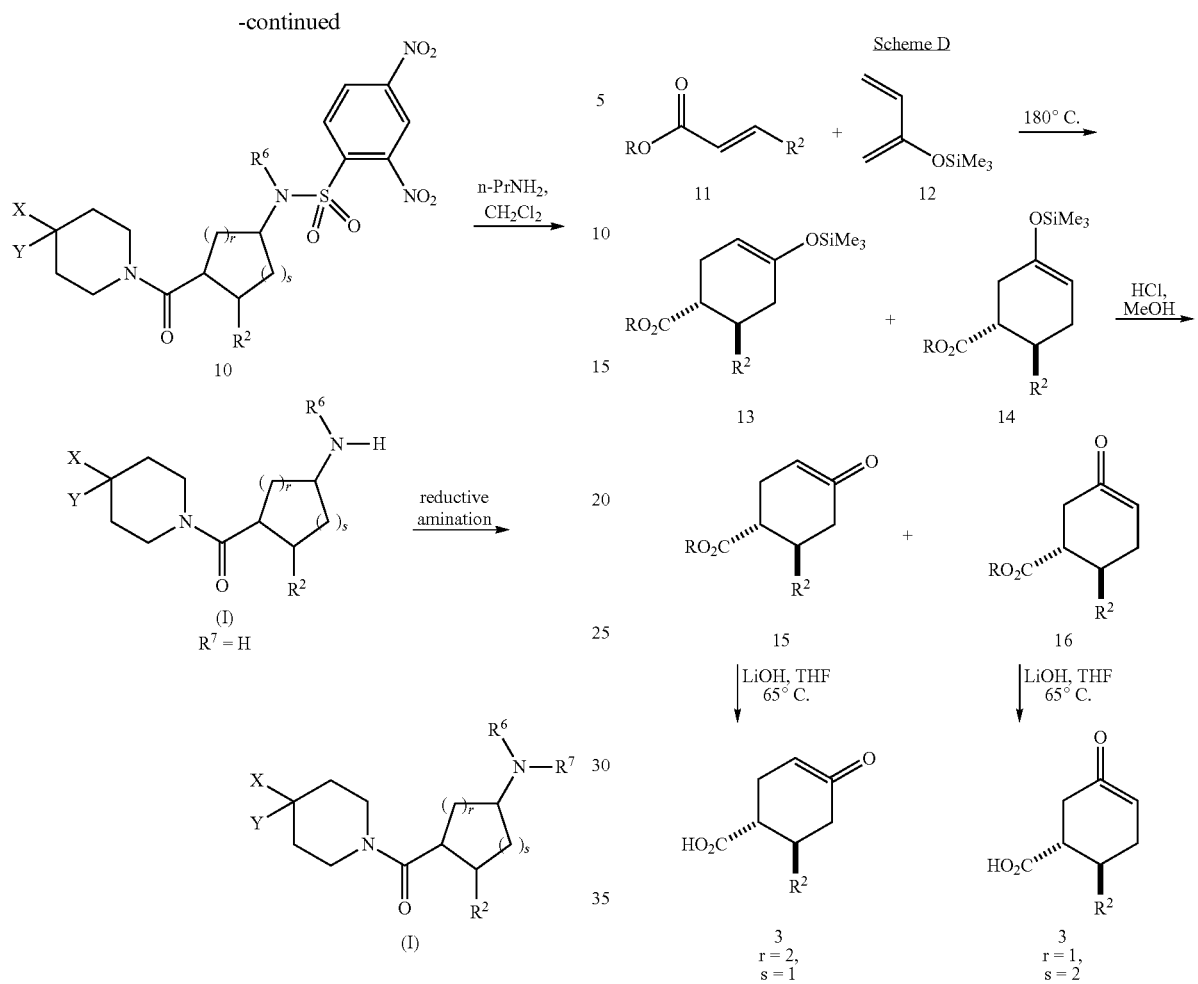

Reaction Scheme D illustrates a preferred method for the synthesis of the cycloalkyl carboxylic acids of general formula 3 when the values of r and s are selected such that the resulting carbocyclic ring is a six-membered ring. In this method a Diels-Alder reaction between an α,β-unsaturated ester of general formula 11 and 2-trimethylsilyloxybutadiene (U) affords a mixture of the two regioisomeric silylenolethers 13 and 14. The silylenolethers 13 and 14 are generally subjected to an hydrolysis reaction using hydrochloric acid in a solvent such as methanol and the two regioisomeric ketones 15 and 16 are then separated by conventional chromatographic methods. The olefin geometry of the starting α,β-unsaturated ester of general formula 11 determines the relative stereochemistry of the two substituents on the six-membered ring. Thus a trans α,β-unsaturated ester (11) affords the trans-disubstituted products 13 and 14 as shown, whereas the corresponding cis isomer of compounds of general formula 11 will afford the corresponding cis isomers of 13 and 14. Once the regioisomeric cyclohexanones of general formulae 15 and 16 are separated, they may then be individually hydrolyzed. For instance, hydrolysis using lithium hydroxide in refluxing tetrahydrofuran, affords the carboxylic acids of general formula 3 (r=2, s=1) and 3 (r=1, s=2). The acids of general formula 3 are finally converted to the novel title compounds of structural formula I using the methodology described above in reaction Scheme B.

Reaction Scheme E illustrates a preferred method for the synthesis of the cycloalkyl carboxylic acids of general formula 3 when the values of r and s are selected such that the resulting carbocyclic ring is a five-membered ring. In this method an α,β-unsaturated ester of general formula 11 is subjected to a trimethylenemethane cycloaddition reaction (Trost, B. M.; Chan, D. M. T. J. Am. Chem. Soc. 1979, 101, 6429) to afford a cyclopentane derivative of general formula 18. The cycloaddition is performed by reacting the α,β-unsaturated ester of general formula 11 with 2-[(trimethylsilyl) methyl]-2-propen-1-yl acetate (17 )in the presence of a palladium(0) catalyst in a solvent such as tetrahydrofuran. A preferred palladium(0) catalyst for the cycloaddition may be generated by mixing palladium acetate and triisopropyl phosphite in the reaction mixture. The cycloaddition reaction is typically conducted at the reflux temperature of the solvent, for instance 65° C., and the reaction is usually completed in periods of 2-8 hours. The olefin geometry of the starting α,β-unsaturated ester of general formula 11 determines the relative stereochemistry of the two substituents on the five-membered ring. Thus a trans α,β-unsaturated ester (11) affords the trans-disubstituted product 18 as shown, whereas the corresponding cis isomer of compounds of general formula 11 affords the corresponding cis-disubstituted isomer of 18. The exocyclic olefin present in compounds of general formula 18 is next oxidatively removed to afford a cyclopentanone derivative of general formula 19. A preferred method for the oxidative cleavage reaction is the two step process shown at the bottom of reaction Scheme E. The methylene cyclopentane derivative of formula 18 is first oxidized to a 1,2-diol derivative using catalytic osmium tetraoxide in the presence of a stoichiometric reoxidant such as N-methylmorpholine-N-oxide and a solvent system such as acetone-water. The intermediate 1,2-diol which forms is generally not isolated, but is in turn subjected to cleavage with sodium periodate in a solvent system like methanol-water to afford ketones of general formula 19. Both steps in the oxidative cleavage sequence are generally completed during periods of several minutes to a few hours and the reaction steps are typically conducted at low temperatures, for instance between 0° C. and room temperature. Alternatively, the oxidative cleavage of olefins of general formula 18 may be accomplished using ozone, or by other methods known in organic synthesis. The cyclopentanones of general formula 19 may then be hydrolyzed, for instance using sodium hydroxide in methanol, to afford the carboxylic acids of general formula 3 (r=1, s=1). The acids of general formula 3 are finally converted to the novel title compounds of structural formula I using the methodology described above in reaction Scheme B.

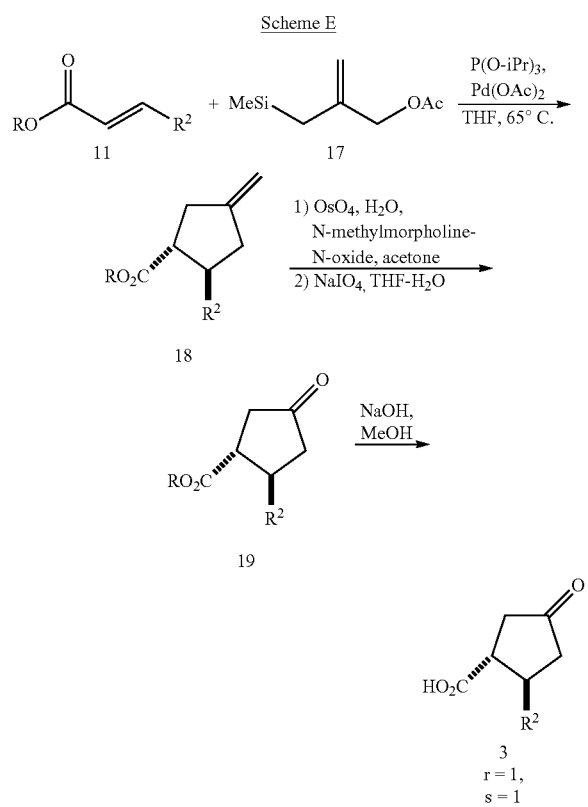

When it is desired to prepare individual enantiomers of the novel title compounds of structural formula I, it is possible to perform a resolution of the compounds of structural formula I using one of the methods known in the art of organic synthesis. For instance, enantiomerically pure compounds (I) may be prepared by crystallization of diastereoisomeric salts formed from the racemic compounds of structural formula I and an optically active carboxylic acid. The two diastereoisomeric salts are separated from each other by fractional crystallization, then the enantiomerically pure compounds of structural formula I are regenerated by treatment of the purified salts with a base. Alternatively, racemic compounds of structural formula I may be resolved by preparative HPLC using commercially available chiral-stationary phase columns. Another strategy for the preparation of enantiomerically pure compounds of structural formula I involves preparing enantiomerically pure compounds of general formula 2 prior to their use in the amide bond forming reaction outlined in reaction Scheme A. Racemic compounds of general formula 2, or intermediates used to prepare compounds of formula 2 as described in the previous reaction Schemes (i.e. acids 3 and 7, or esters 15, 16 and 19) may also be resolved using the classical methods previously discussed.

Enantiomerically pure compounds may also be prepared from starting materials bearing a suitable covalently attached chiral auxiliary group using synthetic transformations similar to those outlined above. Reaction Scheme F illustrates the use of a covalently attached chiral oxazolidinone auxiliary for the preparation of enantiomerically pure cyclopentanones of general formula 19. In this method of preparation, an α,β-unsaturated acyloxazolidone of general formula 20 is subjected to the trimethylenemethane cycloaddition reaction with compound 17 as described above in reaction Scheme E. The α,β-unsaturated acyloxazolidones of general formula 20 are readily prepared from α,β-unsaturated carboxylic acids and (S)-(−)-4-benzyl-2-oxazolidinone using published methodology (Ho, G. -J.; Mathre, D. J. *J. Org. Chem.* 1995, 60, 2271 and references cited therein). The compounds of general formula 20 undergo the trimethylenemethane cycloaddition under the same conditions as compounds of general formula 11 (Scheme E) and the products are the diastereoisomeric cyclopentanes 21 and 22. Compounds of general formulae 21 and 22 are readily separated from each other by chromatographic methods or by recrystallization, and may then be converted to the compounds of general formula 19 individually. This process is illustrated at the bottom of reaction Scheme P for the case of the cyclopentane with the absolute stereochemistry shown in formula 21. The enantiomerically pure compounds of general formula 21 are first hydrolyzed to afford intermediate carboxylic acids and (S)-(−)-4-benzyl-2-oxazolidinone using a reagent such as lithium hydroperoxide in a suitable solvent system such as aqueous tetrahydrofuran. The carboxylic acid formed is generally then converted to a methyl ester 23 using diazomethane, trimethylsilyldiazomethane or any of the esterification methods commonly employed in organic synthesis. The olefin present in the esters of general formula 23 is then subjected to the oxidative cleavage reaction presented in the discussion of reaction Scheme E to afford enantiomerically pure compounds of general formula 19. The compounds of general formula 19 may then be converted into enantiomerically pure compounds of structural formula I as discussed previously.

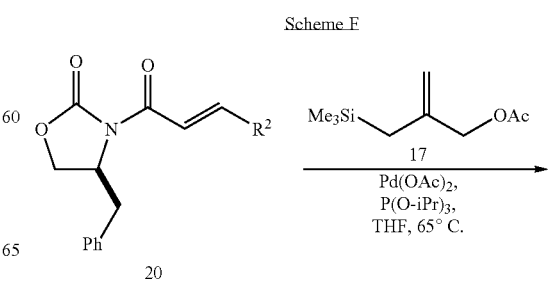

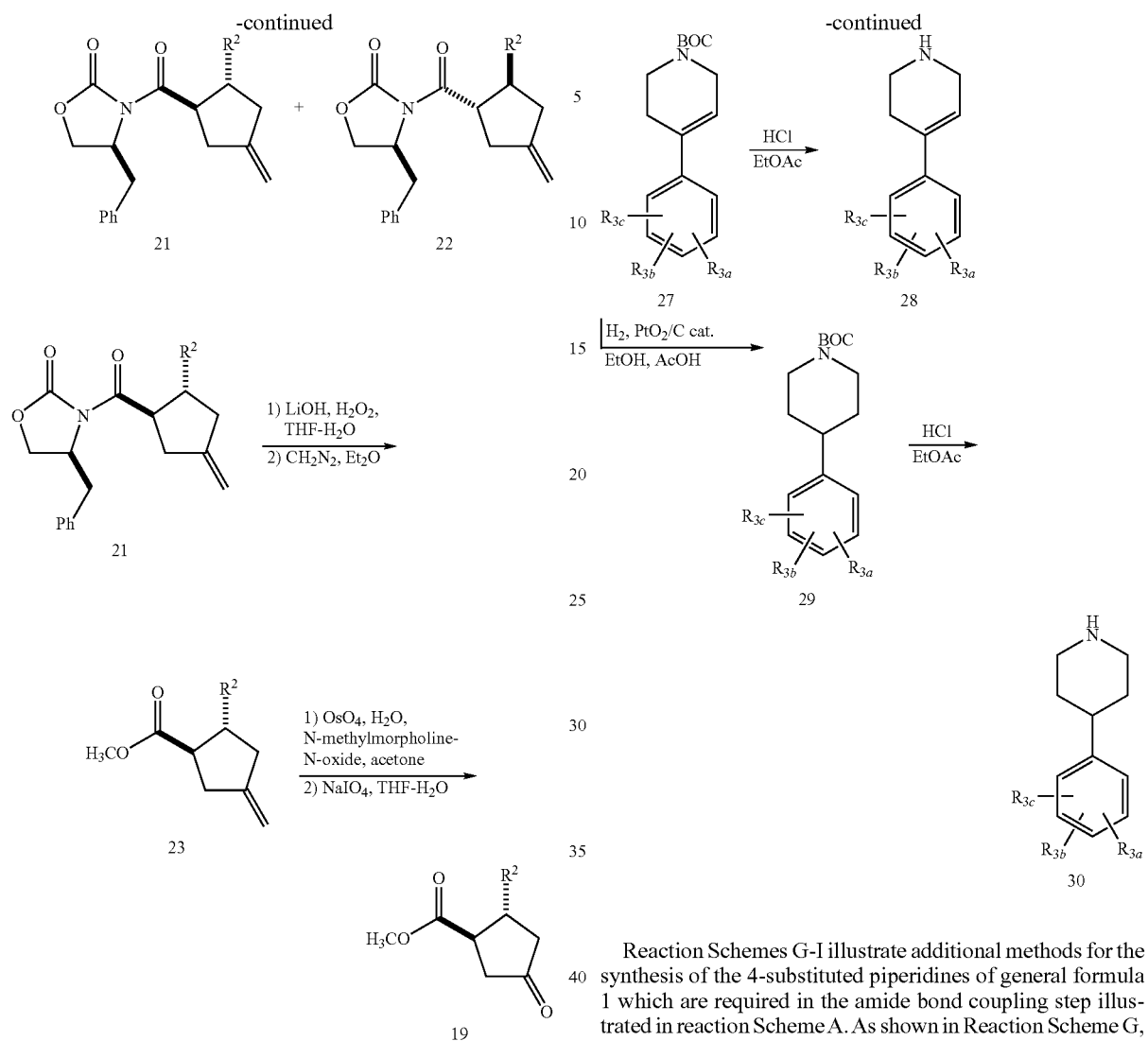

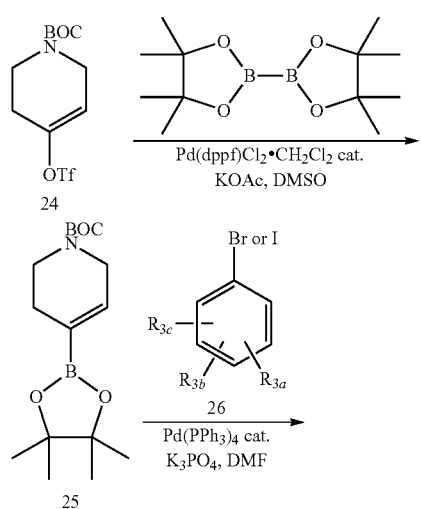

Reaction Schemes G-I illustrate additional methods for the synthesis of the 4-substituted piperidines of general formula 1 which are required in the amide bond coupling step illustrated in reaction Scheme A. As shown in Reaction Scheme G, treatment of enoltriflate 24 (prepared as described in: Rohr, M.; Chayer, S.; Garrido, F.; Mann, A.; Taddei, M.; Wermuth, C-G. *Heterocycles* 1996, 43, 2131-2138.) with bis(pinacolato)diboron reagent in the presence of a suitable palladium (II) catalyst such as [1,1'-bis(diphenylphosphino)-ferrocene] dichloropalladium (II) (Pd(dppf)Cl$_2$) and potassium acetate in a polar, inert organic solvent such as methyl sulfoxide at about 80° C. under an inert atmosphere for a period of 6-24 hours provided the vinyl dioxaborolane 25. Borolane 25 can be further reacted with an aryl halide such as 26 in the presence of a palladium catalyst such as tetrakis(triphenylphosphine)palladium (0) (Pd(Ph$_3$)$_4$) and potassium phosphate in an inert solvent such as N,N-dimethylformamide to give the coupled 4-aryl tetrahydropyridine product 27. The tert-butyloxycarbonyl protecting group can be removed by any of the known methods. such as treatment with a protic acid such as hydrogen chloride in an inert organic solvent such as ethyl acetate or trifluoroacetic acid in methylene chloride to give amine 28. Alternatively, it is sometimes desirable to reduce the double bond in synthetic intermediate 27. This can be effected by treatment with hydrogen at atmospheric or elevated pressure and a noble metal catalyst on carbon such as palladium (0) or platinum(IV) oxide in an inert organic solvent such as ethanol, ethyl acetate, acetic acid or mixtures thereof to give the 4-arylpiperidine 29. Removal of the tertbutyloxycarbonyl protecting group as described above provides amine 30. Both amine intermediates, 28 and 30, may be used as coupling partners in Reaction Scheme A.

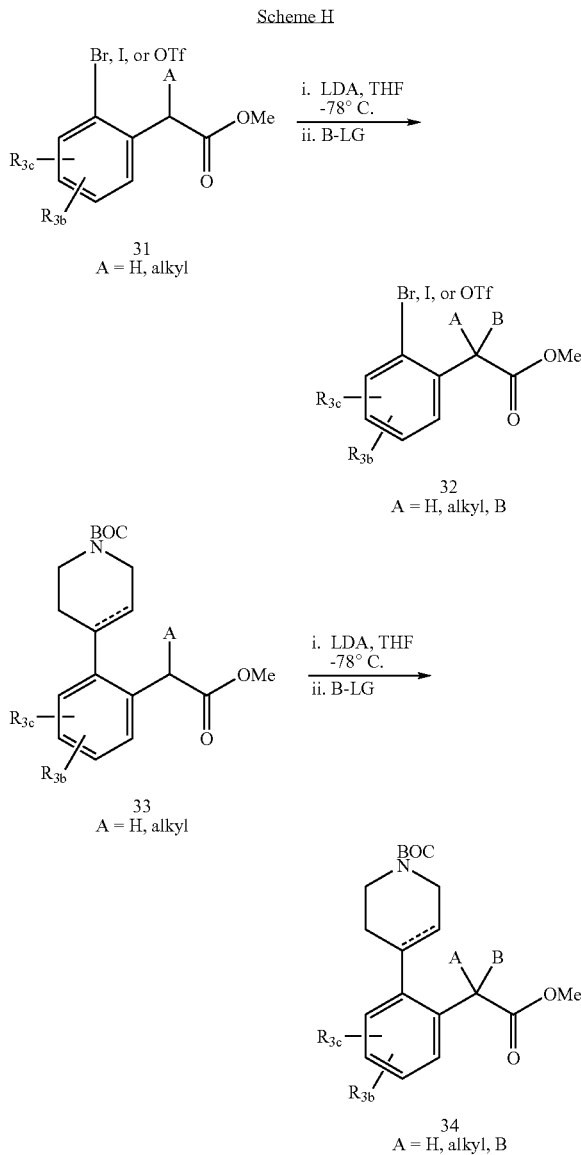

As shown in Reaction Scheme H, aryl groups containing substituents with acidic hydrogens (e.g. 31 and 33) can modified by alkylation under known protocols. For instance, treatment of esters 31 or 33 with a strong base such a lithium diisopropylamide at low temperature in an inert organic solvent such as tetrahydrofuran can form an intermediate enolate which can be reacted in a second step with any alkylating agent (B-LG) such as iodomethane, iodoethane, 1,2-dibromoethane or the like to form the corresponding alkylated product. in addition to ester groups, related amides and functionalities that promote the formation of a stable anion can be alkylated under similar protocols.

Ester intermediates such as 32 and 34 may be further modified by conversion to the corresponding carboxylic acids and coupled with amines to form amides as described in Reaction Scheme I. Conversion of the methyl esters 32 and 34 to the carboxylic acid can be effected by dealkylation using potassium trimethylsilanolate at room temperature in an inert organic solvent such as tetrahydrofuran for a period of about one to about 24 hours to provide, after acidification, the corresponding carboxylic acids. In certain cases, a base-catalyzed hydrolysis known to those skilled in the art may be used to effect this same transformation. These acids may be reacted further to form amides by treatment with a primary or secondary amine under a variety of amide coupling protocols such as described in Scheme A to provide intermediates 35 and 36.

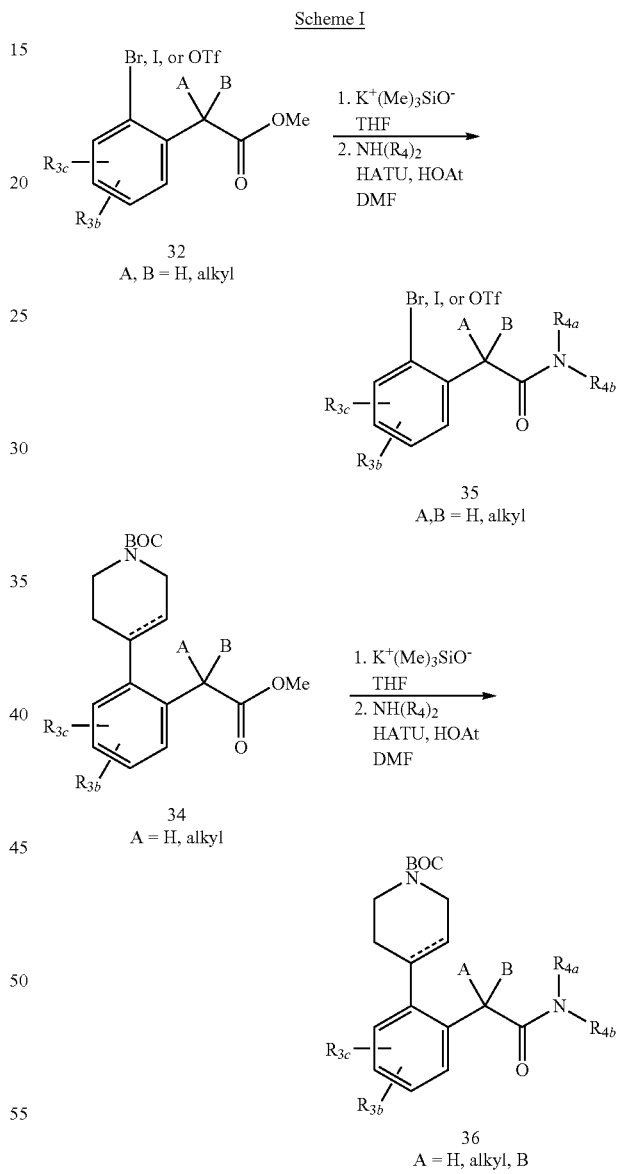

Preparation of 4-Substituted Piperidine Intermediates:

The preparation of other 4-substituted piperidine intermediates of general formula 1 for coupling with the carboxylic acids of general formula 2 as shown in Scheme A below is disclosed in WO 00/74679 (14 Dec. 2000), which is incorporated by reference herein in its entirety. The preparation of additional 4-substituted piperidine intermediates needed to derive the compounds of the present invention is provided below.

Piperidine Intermediate 1:

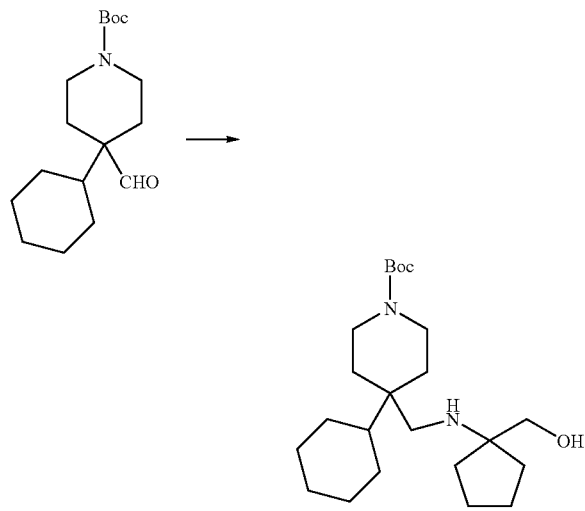

To a solution of 4-cyclohexyl 4-formyl-N-(tertbutyloxycarbonyl)-piperidine (2.56 g, 8.68 mmol) in toluene (100 ml) was added acetic acid (2 ml) and 1-amino-1-cyclopentanemethanol (1.0 g, 8.68 mmol). After refluxing by using a Dean-Stark apparatus for 11 hours, the reaction mixture was concentrated. The residue was dissolved in acetic acid (70 ml) and hydrogenated overnight in the presence of platinum oxide (500 mg) under a balloon atmosphere of hydrogen gas. The catalyst was filtered off and solvent was removed to give a colorless oil, which was dissolved in methanol and made basic by addition of NaOH (5N, 4 ml) and concentrated. The residue was partitioned between water and $CH_2Cl_2$, the two layers separated, and the aqueous layer extracted with $CH_2Cl_2$. The combined organic extracts were washed with brine, dried over $MgSO_4$ and concentrated to give the title compound as a colorless oil (2.1 g).

MS: calc. for $C_{23}H_{42}N_2O_3$: 394.3; Found: 395 (M+1), 417 (M+Na).

Piperidine Intermediate 2:

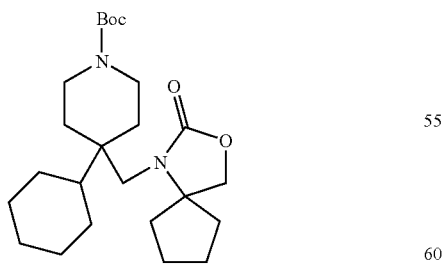

To a solution of Intermediate 1 (2.1 g, 5.33 mmol) in $CH_2Cl_2$ (70 ml) at 0° was added DMAP (0.65 g, 5.33 mmol), DIEA (3.76 ml, 21.3 mmol) followed by slow addition of phosgene (4.1 ml, 8.0 mmol). After stirring the reaction mixture for one hour at 0° C., the ice-water bath was removed and the reaction mixture was continued to stir at room temperature overnight. The mixture was diluted with $CH_2Cl_2$, washed with water and brine, dried over $MgSO_4$ and concentrated to give crude product, which was purified by column chromatography on silica gel (2% $EtOAc/CH_2Cl_2$ to 5% $EtOAc/CH_2Cl_2$) to give the title compound as a white solid (1.2 g).

MS: calc. for $C_{24}H_{40}N_2O_4$: 420.3; Found: (M+1), (M+Na).

Piperidine Intermediate 3:

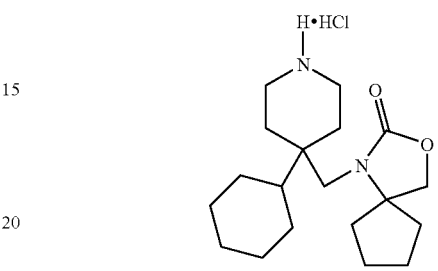

To the Intermediate 2 (1.2 g) was added hydrogen chloride (4.0 M in dioxane). The reaction mixture was stirred at room temperature for 30 minutes and the solvent was removed in vacuo to afford the title compound (1.2 g).

MS: calc. for $C_{19}H_{32}N_2O_2$: 320.3; Found: 321.1 (M+H).

Piperidine Intermediate 4:

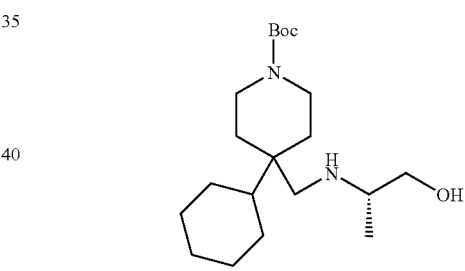

Intermediate 4 was prepared from (S)-(+)-2-amino-1-propanol in an analogous manner to the one described for the preparation of Intermediate 1.

MS: calc. for $C_{20}H_{38}N_2O_3$: 354; Found: 355 (M+H).

Piperidine Intermediate 5:

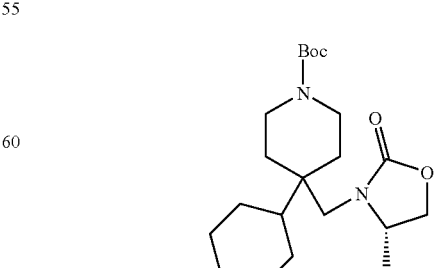

Intermediate 5 was prepared from Intermediate 4 in an analogous manner to the one described for the preparation of Intermediate 2.

MS: calc. for $C_{21}H_{36}N_2O_4$: 380.3; Found: 381 (M+H).

Piperidine Intermediate 6:

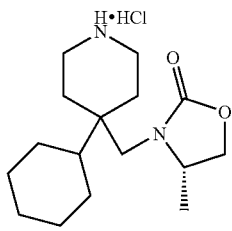

Intermediate 6 was prepared from Intermediate 5 in an analogous manner to the one described for the preparation of Intermediate 3.

MS: calc. for $C_{16}H_{28}N_2O_2$: 280.3; Found: 281 (M+H).

Piperdine Intermediate 7:

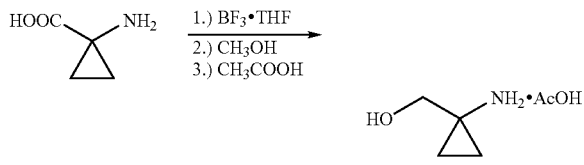

To a suspension of 1-aminocyclopropane-1-carboxylic acid (2.8 g, 27.7 mmol) in THF (20 ml) was added borane-tetrahydrofuran complex (100 ml, 100 mmol) slowly under nitrogen at room temperature. The reaction mixture was stirred at 70° C. overnight, then cooled to 0° C. After addition of methanol (12.2 ml, 300 mmol), the mixture was allowed to stir for 30 minutes. Then acetic acid (1.6 ml, 27.7 mmol) was added. The reaction mixture was concentrated to provide the title compound as a colorless oil (3.0 g).

Piperidine Intermediate 8:

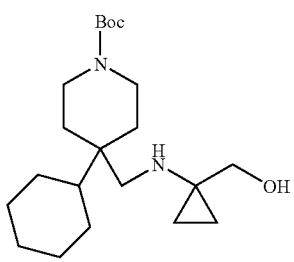

Intermediate 8 was prepared from Intermediate 7 in an analogous manner to the one described for the preparation of Intermediate 1.

MS: calc. for $C_{21}H_{38}N_2O_3$: 366.3; Found: 367 (M+H).

Piperidine Intermediate 9:

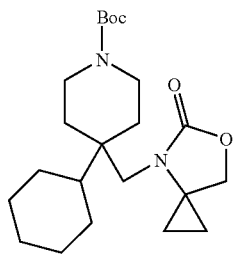

To a solution of Intermediate 8 (0.8 g, 2.18 mmol) in $CH_2Cl_2$ (40 ml) at 0° was added DMAP (0.266 g, 2.18 mmol), DIEA (1.52 ml, 8.74 mmol) and triphosgene (0.648 g, 2.18 mmol). After stirring the reaction mixture for one hour at 0° C., the ice-water bath was removed and the reaction mixture was allowed to stir at r.t. overnight. The mixture was diluted with $CH_2Cl_2$, washed with water and brine, dried over $MgSO_4$ and concentrated to give crude product, which was purified by column chromatography on silica gel (10% $CH_2Cl_2$/EtOAc) to give the title compound as a colorless oil (0.13 g).

ESI-MS: calc. for $C_{22}H_{36}N_2O_4$: 392; Found: 393 (M+1).

Piperidine Intermediate 10:

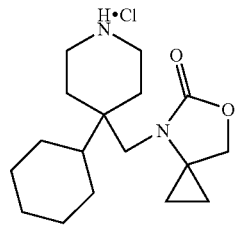

Intermediate 10 was prepared from Intermediate 9 in an analogous manner to the one described for the preparation of Intermediate 3.

MS: calc. for $C_{17}H_{28}N_2O_2$: 292.2; Found: 293 (M+H).

Piperidine Intermediate 11:

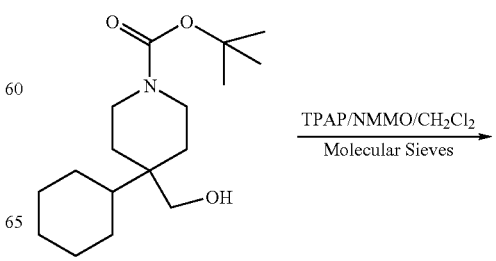

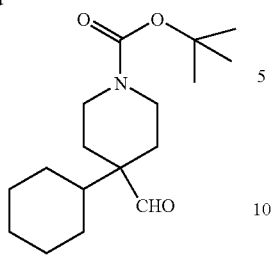

To a solution of the alcohol (9.41 g, 31.6 mmol) in CH$_2$Cl$_2$ (100 ml) at 0° C. containing molecular sieves (2 g) and 4-methylmorpholine N-oxide (NMMO) (4.449 g, 37.98 mmol) was added TPAP (1.12 g, 3.16 mmol). After stirring the reaction mixture at 0° C. for 0.5 h, the reaction mixture was warmed to room temperature and stirred further for 5 hrs. The reaction mixture was concentrated to half the volume, diluted with hexane (250 ml), filtered through a silica gel pad and concentrated to give pure title compound (9.4 g).

Piperidine Intermediate 12:

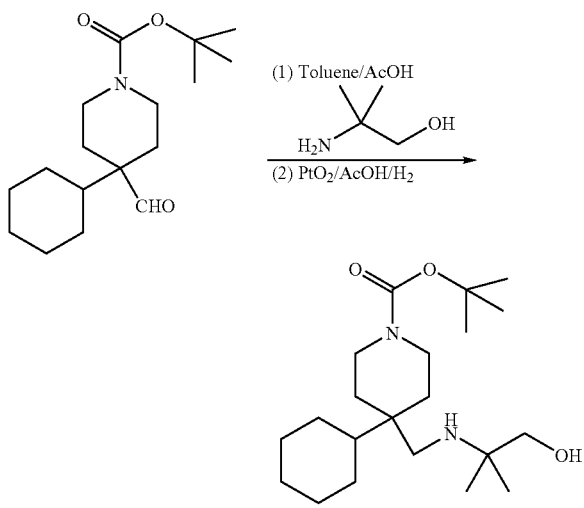

To a solution of the aldehyde (2 g, 6.7 mmol) in toluene (50 ml) was added acetic acid (500 µl). After stirring the reaction mixture at reflux temperature using Dean Stark apparatus for 8 hrs, the mixture was concentrated and dissolved in acetic acid (30 ml). To the mixture was added PtO$_2$ (500 mg) which was stirred under an atmosphere of H$_2$ overnight. The rection mixture was flushed with nitrogen, filtered and concentrated to give the title compound (2 g).

Piperidine Intermediate 13:

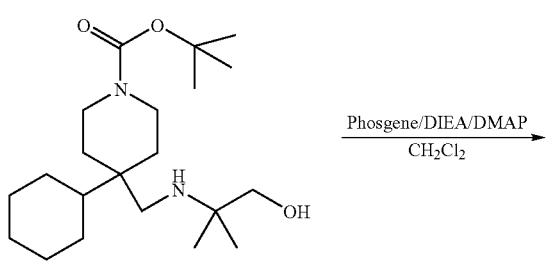

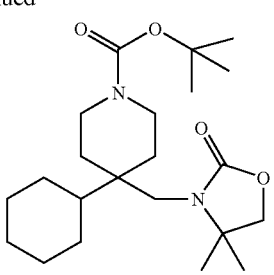

To a solution of the amino alcohol (4.96 g, 13.47 mmol) in CH$_2$Cl$_2$ at 0° C. containing DIEA (6.98 g, 53.9 mmol), DMAP (1.64 g, 13.47 mmol) was added slowly a toluene solution of phosgene (1.93M, 10.47 ml, 20.21 mmol). After stirring the reaction mixture for 1 hr at 0° C., the temperature was raised to room temperature and stirred further for 2 hrs. The reaction mixture was diluted with CH$_2$Cl$_2$, washed with water, brine, dried and concentrated. The residue was purified by column chromatography over silica gel (5% EtOAc/CH$_2$Cl$_2$) to give pure product (3.95 g).

Piperidine Intermediate 14:

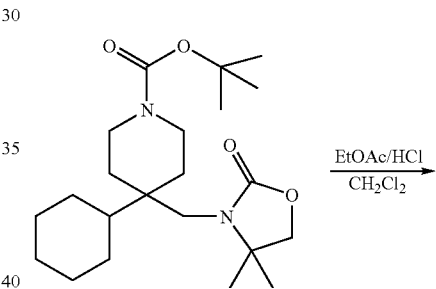

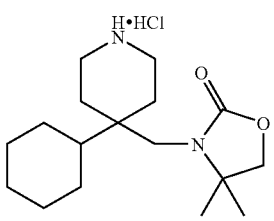

To a solution of Intermediate 13 (3.95 g) in CH$_2$Cl$_2$ was added 5 ml of a saturated HCl solution of EtOAc. After stirring the reaction mixture for 30 minutes at room temperature, the solvent was removed and the residue lyophilized from a benzene/methanol solution to afford the title compound (3.85 g).

The following Examples are provided to illustrate the invention and are not to be construed as limiting the scope of the invention in any manner.

EXAMPLES 1 AND 2

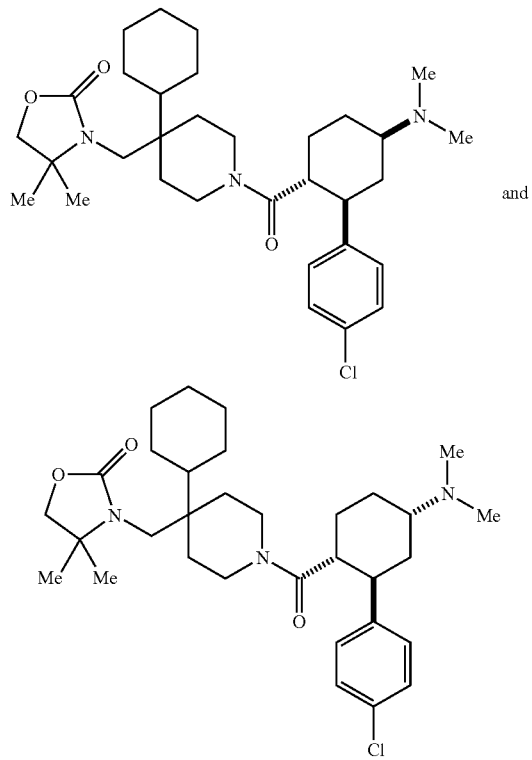

(±)-3-[(1-{[(1R,2R,4R and 1S,2S,4S)-2-(4-chlorophenyl)-4-(dimethlamino)cyclohexyl]carbonyl}-4-cyclohexylpiperidin-4-yl)methyl]-4,4-dimethyl-1,3-oxazolidin-2-one and (±)-3-[(1-{[(1R,2R,4S and 1S,2S,4R)-2-(4-chlorophenyl)-4-(dimethylamino)cyclohexyl]carbonyl}-4-cyclobexylpiperidin-4-yl)methyl]-4,4-dimethyl-1,3-oxazolidin-2-one Step A: Preparation of methyl (±)-trans-6-(4-chlorophenyl)-4-[(trimethylsilyl)oxy]cyclohex-3-ene-1-carboxylate and methyl (±)-trans-6-(4-chlorophenyl)-3-[(trimethylsilyl)oxy]cyclohex-3-ene-1-carboxylate A mixture of methyl (2E)-3-(4-chlorophenyl)prop-2-enoate (2.83 g, 14.4 mmol), 2-trimethylsilyloxy-1,3-butadiene (8.20 g, 57.6 mmol) and hydroquinone (79.3 mg, 0.720 mmol) was heated in a thick-walled glass tube for 2 days at approximately 170° C. After cooling to room temperature, the reaction mixture was purified by flash chromatography on silica gel (gradient elution; 0-20% ethyl acetate/hexanes as eluent) to give a crude regioisomeric mixture of the two title compounds which was used without further purification in the subsequent reaction.

Step B: Preparation of methyl (±)-trans-2-(4-chlorophenyl)-5-oxocyclohexanecarboxylate and methyl trans-2-(4-chlorophenyl)-4-oxocyclohexanecarboxylate 2N Hydrochloric acid (10 mL) was added to a stirred solution of the products from Step A (14.4 mmol) in methanol (10 mL) at room temperature. After approximately 30 min, the reaction mixture was poured into water/brine (1:1) and extracted three times with methylene chloride. The combined organic extracts were washed with brine, dried (MgSO$_4$) and concentrated in vacuo. Purification of the crude residue by mediumpressure liquid chromatography on silica gel (gradient elution; 0-40% ethyl acetate/hexanes as eluent) gave in order of elution, methyl trans-2-(4-chlorophenyl)-5-oxocyclohexanecarboxylate as a colorless solid (0.435 g) followed by methyl trans-2-(4-chlorophenyl)-4-oxocyclohexanecarboxylate as a colorless solid (1.05 g).

Step C: Preparation of (±)-trans-2-(4-chlorophenyl)-4-oxocyclohexanecarboxylic acid A stirred mixture of methyl trans-2-(4-chlorophenyl)-4-oxocyclohexanecarboxylate (1.05 g, 3.94 mmol) and 1 N lithium hydroxide (5.91 mL, 5.91 mmol) in tetrahydrofuran (5 mL) was heated at reflux for approximately 1 h. After cooling to room temperature, the reaction mixture was poured into 1 N hydrochloric acid/brine (1:1) and extracted three times with methylene chloride. The combined organic extracts were washed with brine, dried (MgSO$_4$) and concentrated in vacuo. The crude title compound was used without further purification in the subsequent reaction.

Step D: Preparation of (±)-3-[(1-{[(1,2-trans)-2-(4-chlorophenyl)-4-oxocyclohexyl]carbonyl}-4-cyclohexylpiperidin-4-yl)methyl]-4,4-dimethyl-1,3-oxazolidin-2-one A 25 mL round bottom flask equipped with a magnetic stir bar was charged with 4-cyclohexyl-4-[(4,4-dimethyl-2-oxo-1,3-oxazolidin -3-yl)methyl]piperidinium chloride (75.0 mg, 0.227 mmol), the product of Step C (57.4 mg, 0.227 mmol), 1-hydroxybenzotriazole (46.0 mg, 0.341 mmol) and 4-methylmorpholine (74.9 μL, 0.681 mmol) in methylene chloride (2.2 mL). To the stirred mixture was added 1-(3-dimethylaminopropyl)-3-ethylcarbodiimide hydrochloride (65.3 mg, 0.341 mmol) at ambient temperature. After approximately 18 h, the reaction mixture was poured into saturated aqueous sodium bicarbonate and extracted three times with methylene chloride. The combined organic extracts were washed with water, brine, dried (Na$_2$SO$_4$) and concentrated in vacuo. Purification of the crude residue by mediumpressure liquid chromatography on silica gel (gradient elution; 50-100% ethyl acetate/hexanes as eluent) furnished the title compound as a pale yellow solid (83.0 mg).

Step E: Preparation of (±)-3-[(1-{[(1R,2R,4R and 1S,2S,4S)-2-(4-chlorophenyl)-4-(dimethylamino)cyclohexyl]carbonyl}-4-cyclohexylpiperidin-4-yl)methyl]-4,4-dimethyl-1,3-oxazolidin-2-one and (±)-3-[(1-{[(1R,2R,4S and 1S,2S,4R)-2-(4-chlorophenyl)-4-(dimethylamino)cyclohexyl]carbonyl}-4-cyclohexylpiperidin-4-yl)methyl]-4,4-dimethyl-1,3-oxazolidin-2-one Titanium tetraisopropoxide (55.8 μL, 0.189 mmol) was added to a stirred solution of the product of Step D (40.0 mg, 75.6 μmol) and dimethylamine (189 μL of a 2M solution in methanol, 0.378 mmol) in tetrahydrofuran (0.8 mL) at room temperature. After approximately 18 h, the reaction mixture was cooled to 0° C. (ice cooling) and sodium borohydride (5.70 mg, 0.151 mmol) was added. After warming to room temperature over 1 h, the reaction was quenched with 1 N hydrochloric acid and stirred vigorously for 10 min. The reaction mixture was poured cautiously into saturated aqueous sodium bicarbonate and extracted three times with methylene chloride. The combined organic extracts were washed with brine, dried (Na$_2$SO$_4$) and concentrated in vacuo. Purification of the crude residue by preparative reversed phase highpressure liquid chromatography on YMC Pack Pro C18 phase (gradient elution; 0-100% acetonitrile/water as eluent, 0.1% TFA as modifier) afforded, in order of elution, the trifluoroacetic acid salt of (±)-(1R,2R,4R and 1S,2S,4S) diastereoisomer as an off-white solid [(14.7 mg), m/z (ES) 558 (MH⁺)] followed by its C-4 epimer, the trifluoroacetic acid salt of (±)-(1R,2R,4S and 1S,2S,4R) as an off-white solid [(10.6 mg), m/z (ES) 558 (MH⁺)].

Following a procedure similar to that described above, the following compounds can be prepared.

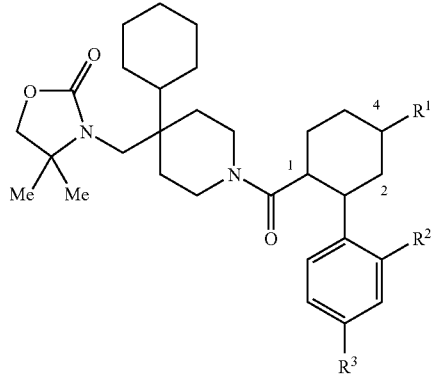

| Ex. # | stereo. (1, 2, 4) | R¹ | R² | R³ | Parent Ion m/z |
|---|---|---|---|---|---|
| 3 | (R, R, R) & (S, S, S) | Me-N(-Me) | —H | —F | 542 |
| 4 | (R, R, R) & (S, S, S) | Me-N(-Me) | —F | —F | |
| 5 | (R, R, R) & (S, S, S) | H-N(-Me) | —H | —F | 528 |
| 6 | (R, R, R) & (S, S, S) | H-N(-Me) | —F | —F | |
| 7 | (R, R, S) & (S, S, R) | H-N(-Me) | —H | —F | 528 |
| 8 | (R, R, S) & (S, S, R) | H-N(-Me) | —F | —F | |
| 9 | (R, R, S) & (S, S, R) | Me-N(-Me) | —H | —F | |
| 10 | (R, R, S) & (S, S, R) | Me-N(-Me) | —F | —F | |
| 11 | (R, R, S) & (S, S, R) | H-N(-Me) | —H | —Cl | 544 |

| Ex. # | stereo. (1, 2, 4) | R¹ | R² | R³ | Parent Ion m/z |
|---|---|---|---|---|---|
| 12 | (R, R, S) & (S, S, R) | H-N(-Me) | —H | —Cl | 544 |
| 13 | (R, R, S) & (S, S, R) | H-N(-Me) | —F | —Cl | |
| 14 | (R, R, S) & (S, S, R) | H-N(-Me) | —F | —Cl | |
| 15 | (R, R, S) & (S, S, R) | Me-N-Et-Me | —H | —Cl | 586 |
| 16 | (R, R, R) & (S, S, S) | Me-N-Et-Me | —H | —Cl | 586 |
| 17 | (R, R, S) & (S, S, R) | azetidinyl-N-Me | —H | —Cl | 570 |
| 18 | (R, R, R) & (S, S, S) | azetidinyl-N-Me | —H | —Cl | 570 |
| 19 | (R, R, S) & (S, S, R) | cyclopropyl-NH-Me | —H | —Cl | 570 |
| 20 | (R, R, R) & (S, S, S) | cyclopropyl-NH-Me | —H | —Cl | 570 |
| 21 | (R, R, S) & (S, S, R) | cyclobutyl-NH-Me | —H | —Cl | 584 |
| 22 | (R, R, R) & (S, S, S) | cyclobutyl-NH-Me | —H | —Cl | 584 |

49
-continued

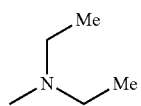

| Ex. # | stereo. (1, 2, 4) | R¹ | R² | R³ | Parent Ion m/z |
|---|---|---|---|---|---|
| 23 | (R, R, S) & (S, S, R) | N(Me)(CH₂CH₂Me)... -N(Me)CH₂CH(Me) with Me groups | —F | —Cl | |
| 24 | (R, R, R) & (S, S, S) | (same as 23) | —F | —Cl | |
| 25 | (R, R, S) & (S, S, R) | N-methyl azetidinyl | —F | —Cl | |
| 26 | (R, R, R) & (S, S, R) | N-methyl azetidinyl | —F | —Cl | |
| 27 | (R, R, S) & (S, S, R) | N-methyl cyclopropylamino | —F | —Cl | |
| 28 | (R, R, R) & (S, S, S) | N-methyl cyclopropylamino | —F | —Cl | |
| 29 | (R, R, S) & (S, S, R) | N-methyl cyclobutylamino | —F | —Cl | |
| 30 | (R, R, R) & (S, S, S) | N-methyl cyclobutylamino | —F | —Cl | |

50
EXAMPLE 31

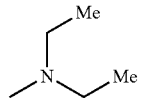

3-[(1-{[(1R,2R,5R)-2-(4-Chlorophenyl)-5-(methylamino)cyclohexyl]carbonyl}-4-cyclohexylpiperidin-4-yl)methyl]-4,4-dimethyl-1,3-oxazolidin-2-one Step A: Preparation of (±)-trans-2-(4-chlorophenyl)-5-oxocyclohexanecarboxylic acid A stirred mixture of 0.435 g (1.63 mmol) of methyl trans-2-(4-chlorophenyl)-5-oxocyclohexanecarboxylate (described in Step B of Example 1) and 1 N lithium hydroxide (3.26 mL, 3.26 mmol) in tetrahydrofuran (3.3 mL) was heated at reflux for approximately 1 h. After cooling to room temperature, the reaction mixture was poured into 1 N hydrochloric acid/brine (1:1) and extracted three times with methylene chloride. The combined organic extracts were washed with brine, dried (MgSO₄) and concentrated in vacuo. The residual crude title compound was used without further purification in the subsequent reaction.

Step B: Preparation of (±)-3-[(1-{[(1,2-trans)-2-(4-chlorophenyl)-5-oxocyclohexyl]carbonyl}-4-cyclohexylpiperidin-4-yl)methyl]-4,4-dimethyl-1,3-oxazolidin-2-one A round bottom flask equipped with a magnetic stir bar was charged with 4-cyclohexyl-4-[(4,4-dimethyl-2-oxo-1,3-oxazolidin-3-yl)methyl]piperidinium chloride (45.0 mg, 0.136 mmol), the product of Step A (34.3 mg, 0.136 mmol), 1-hydroxybenzotriazole (27.6 mg, 0.204 mmol) and 4-methylmorpholine (44.9 µL, 0.408 mmol) in methylene chloride (2.2 mL). To the stirred mixture was added 1-(3-dimethylaminopropyl)-3-ethylcarbodiimide hydrochloride (39.1 mg, 0.204 mmol) at ambient temperature. After approximately 18 h, the reaction mixture was poured into saturated aqueous sodium bicarbonate and extracted three times with methylene chloride. The combined organic extracts were washed with water, brine, dried (Na₂SO₄) and concentrated in vacuo. Purification of the crude residue by mediumpressure liquid chromatography on silica gel (gradient elution; 50-100% ethyl acetate/hexanes as eluent) furnished the title compound as a colorless solid (42.0 mg).

Step C: Preparation of (±)-3-[(1-{[(1R,2R,5R and 1S,2S,5S)-2-(4-chlorophenyl)-5-(methylamino)cyclohexyl]carbonyl}-4-cyclohexylpiperidinyl)-4-yl)methyl]4,4-dimethyl-1,3-oxazolidin-2-one Titanium tetraisopropoxide (58.6 µL, 0.199 mmol;) was added to a stirred solution of the product of Step B (42.0 mg, 79.4 µmol) and methylamine (199 µL of a 2 M solution in methanol, 0.397 mmol) in methanol (0.8 mL) at room temperature. After approximately 18 h, the reaction mixture was cooled to −10° C. (ice cooling) and sodium borohydride (7.50 mg, 0.199 mmol) was added. After warming to room temperature over 1 h, the reaction was quenched with 1 N hydrochloric acid and stirred vigorously for 10 min. The reaction mixture was poured cautiously into saturated aqueous sodium bicarbonate and extracted three times with methylene chloride. The combined organic extracts were washed with brine, dried ($Na_2SO_4$) and concentrated in vacuo. Purification of the crude residue by preparative reversed phase highpressure liquid chromatography on YMC Pack Pro C18 phase; 0-100% acetonitrile/water as eluent, 0.1% TFA as modifier) afforded the trifluoroacetic acid salt of the title compound as an off-white solid [(10.5 mg), m/z (ES) 544 ($MH^+$)].

Following a procedure similar to that described above, the following compounds can be prepared:

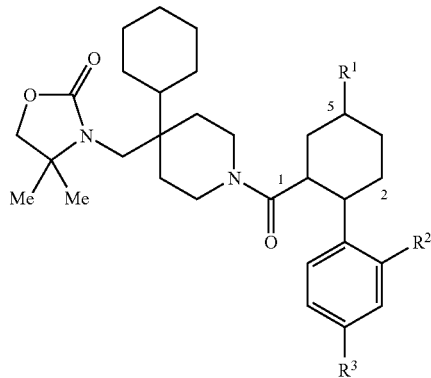

| Ex. # | stereo. (1, 2, 5) | $R^1$ | $R^2$ | $R^3$ | Parent Ion m/z |
|---|---|---|---|---|---|
| 32 | (R, R, R) & (S, S, S) | NHMe (iPr) | —H | —F | 528 |
| 33 | (R, R, R) & (S, S, S) | NHMe (iPr) | —F | —F | |
| 34 | (R, R, R) & (S, S, S) | NHMe (iPr) | —F | —Cl | |
| 35 | (R, R, R) & (S, S, S) | NMe₂ (iPr) | —H | —Cl | |
| 36 | (R, R, R) & (S, S, S) | NMe₂ (iPr) | —H | —F | |
| 37 | (R, R, R) & (S, S, S) | NMe₂ (iPr) | —F | —Cl | |
| 38 | (R, R, R) & (S, S, S) | NMe₂ (iPr) | —F | —F | |
| 39 | (R, R, R) & (S, S, S) | NHMe (iPr) | —H | —Cl | 572 |
| 40 | (R, R, R) & (S, S, S) | NHMe (iPr) | —H | —F | |
| 41 | (R, R, R) & (S, S, S) | NHMe (iPr) | —F | —Cl | |
| 42 | (R, R, R) & (S, S, S) | NHMe (iPr) | —F | —F | |

EXAMPLE 43

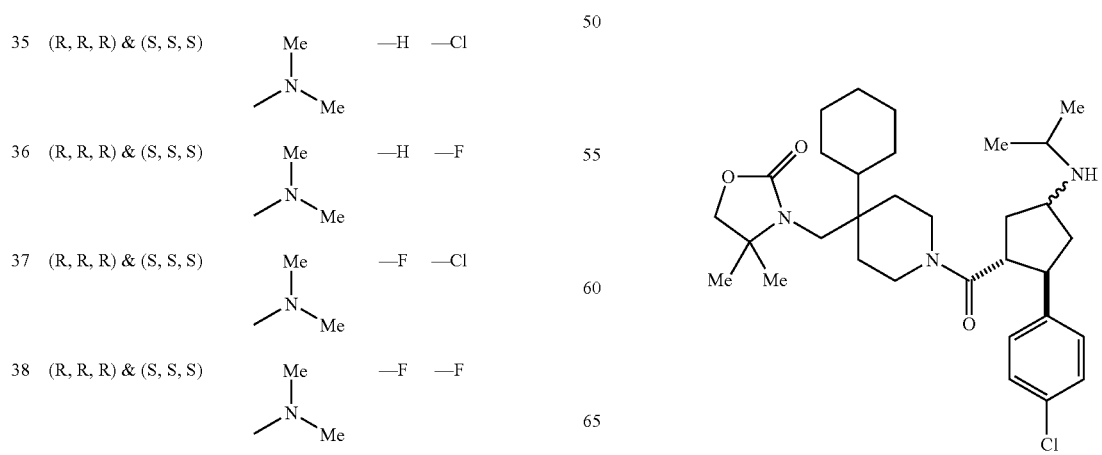

3-[(1-{[(1R,2R)-2-(4-Chlorophenyl)-4-(isopropylamino)cyclopentyl]carbonyl}-4-cyclohexylpiperidin-4-yl)methyl]-4,4-dimethyl-1,3-oxazolidin-2-one Step A: Preparation of (S)-4-benzyl-3-[(2E)-3-(4-chlorophenyl)prop-2-enoyl]-1,3-oxazolidin-2-one An oven-dried, three-necked, 1 L 24/40 round-bottom flask equipped with a mechanical stirrer, a septum and a nitrogen inlet was charged with a solution of 20.00 g (0.110 mol) of 4-chlorocinnamic acid in 400 mL of anhydrous tetrahydrofuran. The reaction mixture was purged with nitrogen and stirred at −20° C. and then 19.93 mL (0.143 mol) of triethylamine and 14.84 mL (0.120 mol) of pivaloyl chloride were added via syringe. The reaction mixture was stirred at −20° C. for 30 min, then at room temperature for 1.5 h. A separate, oven-dried, three-necked, 2 L 24/40 round-bottom flask was equipped with a mechanical stirrer, and a nitrogen inlet. The contents were purged with nitrogen gas and then charged with 16.243 g (0.092 mol) of (S)-(−)-4-benzyl-2-oxazolidinone, 4.274 g (0.101 mol) of finely powdered anhydrous lithium chloride, 400 mL of anhydrous tetrahydrofuran and 16.61 mL (0.119 mol) of triethylamine. The reaction flask was fitted with an oven-dried fritted vacuum filtration funnel in one of its necks, and the reaction mixture was stirred at −20° C. The mixed anhydride prepared in the first reaction flask was separated from precipitated triethylamine hydrochloride by rapid filtration into the second flask with the aid of a slight vacuum applied to the filtration funnel. The reaction mixture in the second flask was again purged with nitrogen, stirred for 30 min at −20° C., then allowed to warm to room temperature and stirred an additional 5 h. At this point the reaction mixture was filtered again and concentrated in vacuo. The crystalline residue was dissolved in methylene chloride, washed with 0.5 M hydrochloric acid, water, saturated aqueous sodium bicarbonate, brine, then dried (MgSO$_4$), filtered and evaporated. The residue was purified by rapid filtration through a six inch bed of silica gel 60 eluted with methylene chloride. Evaporation of the purified fractions and drying in vacuo afforded 23.38 g of the title compound.

Step B: Preparation of (4S)-4-benzyl-3-{[(1R,2R)-2-(4-chlorophenyl)-4-methylenecyclopentyl]carbonyl}-1,3-oxazolidin-2-one An oven-dried 250 mL round bottom flask equipped with a magnetic stir bar and a septum was charged with 4.705 g (13.7 mmol) of the product of Step A, 0.185 g (0.82 mmol) of palladium acetate, and 27 mL anhydrous tetrahydrofuran. The reaction mixture was freed of air by alternate cycles of degassing in vacuo and flushing with nitrogen using an external manifold attached through tubing to a needle inserted through the septum of the flask. To the brick red suspension was then added 3.80 mL (3.334 g, 17.9 mmol) 2-[(trimethylsilyl)methyl]-2-propen-1-yl acetate followed by 1.02 mL (0.860 g, 4.13 mmol) of triisopropyl phosphite. The reaction mixture was heated to reflux and stirred under nitrogen for 3 h at which point TLC analysis (15% ethyl acetate-hexanes) revealed consumption of the starting material and production of two new products. The reaction mixture was cooled to room temperature, transferred to a separatory funnel and partitioned between water and diethyl ether. The organic layer was washed with water, brine, dried (MgSO$_4$), filtered and evaporated in vacuo. The product mixture was purified on a Biotage Flash 40i chromatography apparatus (90 g Flash 40M silica gel cartridge) eluted with 10% ethyl acetate-hexanes which afforded a less polar and a more polar product. Evaporation of the fractions containing the more polar product and drying in vacuo afforded 2.12 g of the title compound.

Step C: Preparation of (4S)-4-benzyl-3-{[(1R,2R)-2-(4chlorophenyl)-4-oxocyclopentyl]carbonyl}-1,3-oxazolidin-2-one A 25 mL round bottom flask equipped with a magnetic stir bar was charged with 1.980 g (5.00 mmol) of the product of Step B dissolved in 9.0 mL acetone. To the reaction mixture was added 0.702 g (5.99 mmol) of 4-methylmorpholine N-oxide dissolved in 2 mL water followed by 1.6 mL (0.26 mmol) of an osmium tetroxide solution (4 wt % in water). The reaction mixture was stirred 1.5 h at room temperature at which point TLC analysis (25% ethyl acetate-hexanes) indicated complete consumption of the starting material. The reaction mixture was quenched with excess 10% aqueous sodium bisulfite, then partitioned between water and ethyl acetate in a separatory funnel. The organic layer was washed with water, separated, then dried (MgSO$_4$), filtered and evaporated in vacuo. The residual oil was redissolved in 12 mL of 1:1 tetrahydrofuran-water in a 25 mL round bottom flask. To this solution was added 1.282 g (5.99 mmol) of sodium periodate and an aditional 3 mL of tetrahydrofuran. After stirring for approximately 30 min at room temperature, a precipitate formed. Stirring was continued for 1.5 h, at which point TLC analysis (50% ethyl acetate-hexanes) revealed a new less polar product spot. The mixture was suspended between ethyl acetate and water and extracted. The organic layer was separated, dried (MgSO$_4$), filtered and evaporated in vacuo. The residual clear oil was used in the next step without further purification.

Step D: Preparation of (1R,2R)-2-(4-chlorophenyl)-4-oxocyclopentanecarboxylic acid A 100 mL round bottom flask equipped with a magnetic stir bar was charged with a solution of 1.002 g (2.52 mmol) of the product of Step C dissolved in 41 mL of tetrahydrofuran followed by the addition of 9 mL of water. The reaction mixture was stirred and cooled to 0° C. with an external ice-water bath and a fine suspension was observed. Lithium hydroxide (0.120 g, 5.02 mmol) was added followed by 1.71 mL (15.1 mmol) of 30% aqueous hydrogen peroxide. The reaction mixture was stirred for 1 h at room temperature during which time it developed a yellow color. The reaction mixture was then quenched by addition of excess saturated aqueous sodium sulfite and the tetrahydrofuran was removed in vacuo. The residue was extracted three times with methylene chloride to remove the oxazolidinone, then the aqueous layer was adjusted to pH=1-2 with 1 N hydrochloric acid. The aqueous layer was then extracted three times with ethyl acetate. The combined organic layers were dried (Na$_2$SO$_4$), filtered and evaporated in vacuo. The residual amorphous yellow solid (0.412 g) was used directly in the next step without further purification.

Step E: Preparation of 3-[(1-{[(1R,2R)-2-(4-chlorophenyl)-4-oxocyclopentyl]carbonyl}cyclohexylpiperidin-4-yl)methyl]-4,4-dimethyl-1,3-oxazolidin-2-one A 25 mL round bottom flask equipped with a magnetic stir bar was charged with 0.412 g (1.73 mmol) of the product of Step D dissolved in 6 mL of methylene chloride. To the reaction mixture was added 0.451 g (2.35 mmol) of 1-(3-dimethylaminopropyl)-3-ethylcarbodiimide hydrochloride, 0.318 g (2.35 mmol) of 1-hydroxybenzotriazole, 0.518 µL (4.71 mmol) of N-methylmorpholine, followed by 0.520 g (1.57 mmol) of 4-cyclohexyl-4-[(4,4-dimethyl-2-oxo -1,3-oxazolidin-3-yl)methyl]piperidinium chloride. The resulting clear yellow solution was stirred at room temperature for 48 h, then was partitioned between methylene chloride and saturated aqueous sodium bicarbonate. The organic layer was separated, washed with 1 N hydrochloric acid, saturated aqueous sodium bicarbonate, brine, then dried ($Na_2SO_4$), filtered and evaporated in vacuo. The residual oil was purified on a Biotage Flash 40i chromatography apparatus (40 g Flash 40S silica gel cartridge) eluted sequentially with hexane for 2 min, 30% ethyl acetate-hexanes for 2 min and finally 75% ethyl acetate-hexanes for 20 min. Evaporation of the purified fractions and drying in vacuo afforded the title compound.

Step F: Preparation of 3-[(1-{[(1R,2R)-2-(4-chlorophenyl)-4-(isopropylamino)cyclopentyl]carbonyl}-4-cyclohexylpiperidin-4-yl)methyl]-4,4-dimethyl-1,3-oxazolidin-2-one Titanium tetraisopropoxide (57.3 μL, 0.194 mmol) was added to a stirred solution of the product of Step E (40.0 mg, 77.7 μmol) and isopropylamine (33.1 μL, 0.388 mmol) in tetrahydrofuran (0.8 mL) at room temperature. After approximately 18 h, the reaction mixture was cooled to 0° C. (ice cooling) and sodium borohydride (7.30 mg, 0.194 mmol) was added. After warming to room temperature over 1 h, the reaction was quenched with 1 N hydrochloric acid and the resulting mixture stirred vigorously for 10 minutes. The reaction mixture was poured cautiously into saturated aqueous sodium bicarbonate and extracted three times with methylene chloride. The combined organic extracts were washed with brine, dried ($Na_2SO_4$) and concentrated in vacuo. Purification of the residue by preparative reversed phase highpressure liquid chromatography on YMC Pack Pro C18 phase (gradient elution; 0-100% acetonitrile/water as eluent, 0.1% TFA as modifier) gave the title compound as an off-white solid [(40.3 mg), m/z (ES) 558 (MH$^+$)].

EXAMPLE 44

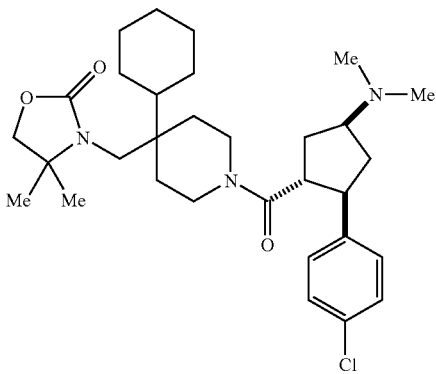

3-[(1-{[(1R,2R,4S)-2-(4-chlorophenyl)-4-(dimethylamino)cyclopentyl]carbonyl}-4-cyclohexylpiperidin-4-yl)methyl]-4,4-dimethyl-1,3-oxazolidin-2-one Step A: Preparation of (1R,2R)-2-(4-chlorophenyl)-4-methylenecyclopentanecarboxylic acid A 100 mL round bottom flask equipped with a magnetic stir bar was charged with a solution of 1.269 g (3.20 mmol) of the product of Step B in Example 43 dissolved in 52 mL of tetrahydrofuran followed by the addition of 13 mL of water. The reaction mixture was stirred and cooled to 0° C. with an external ice-water bath. Lithium hydroxide (0.152 g, 6.36 mmol) was added followed by 2.18 mL (19.2 mmol) of 30% aqueous hydrogen peroxide. The reaction mixture was stirred for 1.5 h at 0° C. then was quenched by addition of excess saturated aqueous sodium sulfite. The reaction mixture was stirred for 10 min at room temperature, then the tetrahydrofuran was removed in vacuo. The residue was extracted three times with methylene chloride to remove the oxazolidinone, then the aqueous layer was adjusted to pH=2 with 1 N hydrochloric acid. The aqueous layer was then extracted three times with ethyl acetate. The combined organic layers were dried ($MgSO_4$), filtered and evaporated in vacuo. The residual colorless oil (780 mg) was used directly in the next step without further purification.

Step B: Preparation of methyl (1R,2R)-2-(4-chlorophenyl)-4-methylenecyclopentanecarboxylate A 100 mL round bottom flask was equipped with a magnetic stir bar and charged with a solution of 1.188 g (5.02 mmol) of the product from Step A (the combined product of two experiments) dissolved in 20 mL of methanol was stirred and cooled to 0° C. with an external ice-water bath. A solution of diazomethane in diethyl ether was added slowly until the reaction mixture developed the persistent yellow color and TLC analysis (25% ethyl acetate-hexanes) indicated that esterification was complete. Excess diazomethane was quenched by dropwise addition of acetic acid, and volatiles were removed in vacuo. The residual clear oil was used directly in the next step without further purification.

Step C: Preparation of methyl (1R,2R)-2-(4-chlorophenyl)-4-oxocyclopentanecarboxylate A 50 mL round bottom flask equipped with a magnetic stir bar was charged with 1.20 g (4.8 mmol) of the product of Step B dissolved in 8.6 mL acetone. To the reaction mixture was added 0.673 g (5.74 mmol) of 4-methylmorpholine N-oxide dissolved in 2 mL water followed by 1.52 mL (0.20 mmol) of an osmium tetroxide solution (4 wt % in water). The reaction mixture was stirred 1 h at room temperature at which point TLC analysis indicated complete consumption of the starting material. The reaction mixture was quenched with excess 10% aqueous sodium bisulfite, then partitioned between water and ethyl acetate in a separatory funnel. The organic layer was washed with water, separated, dried ($MgSO_4$), filtered and evaporated in vacuo. The residual oil was redissolved in 5.5 mL tetrahydrofuran in a 25 mL round bottom flask and 5.5 mL water was added. To this solution was added 1.228 g (5.74 mmol) of sodium periodate. After stirring for approximately 10 min at room temperature, a precipitate formed and the suspension was diluted with 5 mL tetrahydrofuran. Stirring was continued for 1 h, at which point TLC analysis revealed a new less polar product spot. The mixture was suspended between ethyl acetate and water and extracted. The organic layer was separated, dried ($MgSO_4$), filtered and evaporated in vacuo. The residual clear oil was used in the next step without further purification.

Step D: Preparation of methyl (1R,2R,4R)-2-(4-chlorophenyl)-4-hydroxycyclopentanecarboxylate A 100 mL round bottom flask equipped with a magnetic stir bar was charged with a solution of 1.907 g (7.55 mmol) of the product of Step C dissolved in 35 mL of methanol. The reaction mixture was stirred and cooled to at 0° C. with an external ice-water bath and 0.314 g of sodium borohydride (8.30 mmol) was added in portions. The reaction was stirred for 1 h and allowed to slowly warm to room temperature at which point TLC analysis (50% ethyl acetate-hexanes) indicated consumption of the starting material and formation of two more polar products. The mixture was diluted with water and extracted three times with chloroform. The organic extracts were combined, washed with brine, dried (MgSO₄), filtered and evaporated in vacuo. The product mixture was purified on an ISCO medium pressure liquid chromatography apparatus (110 g silica gel cartridge) eluted sequentially with hexane for 2 min, 40% ethyl acetate-hexanes for 20 min and finally 60% ethyl acetate-hexanes for 40 min which afforded two epimeric alcohols. Evaporation of the more polar product and drying in vacuo afforded the title compound. The relative stereochemical assignment for each alcohol was made using nuclear Overhauser effect nmr spectroscopic analysis.

Step E: Preparation of (1R,2R,4R)-2-(4-chlorophenyl)-4-hydroxycyclopentanecarboxylic acid A 25 mL round bottom flask equipped with a magnetic stir bar was charged with 0.320 g (1.26 mmol) of the product of Step D dissolved in 12 mL methanol. Aqueous sodium hydroxide (2.5 mL, 2.5 M; 6.25 mmol) was added and the reaction mixture was stirred and heated to 65° C. in an oil bath. After 1.5 h, TLC analysis (50% ethyl acetate-hexanes) indicated complete hydrolysis. The reaction mixture was cooled to room temperature, transferred to a separatory funnel and partitioned between methylene chloride and water. The organic layer was separated, washed with 1 N hydrochloric acid, brine, then dried (MgSO₄), filtered and evaporated in vacuo. The residual product was used in the next step without further purification.

Step F: Preparation of 3-[(1-{[(1R,2R,4R)-2-(4-chlorophenyl)-4-hydroxycyclopentyl]carbonyl}-4-cyclohexylpiperidin-4-yl)methyl]-4,4-dimethyl-1,3-oxazolidin-2-one A 25 mL round bottom flask equipped with a magnetic stir bar was charged with 0.285 g (1.18 mmol) of the product of Step E dissolved in 4 mL of methylene chloride. To the reaction mixture was added 0.340 g (1.77 mmol) of 1-(3-dimethylaminopropyl)-3-ethylcarbodiimide hydrochloride, 0.240 g (1.78 mmol) of 1-hydroxybenzotriazole, 0.390 μL (3.55 mmol) of N-methylmorpholine, followed by 0.431 g (1.30 mmol) of 4-cyclohexyl-4-[(4,4-dimethyl-2-oxo -1,3-oxazolidin-3-yl)methyl]piperidinium chloride. The resulting solution was stirred at room temperature for 48 h, then was partitioned between methylene chloride and saturated aqueous sodium bicarbonate. The organic layer was separated, washed with 1 N hydrochloric acid, saturated aqueous sodium bicarbonate, brine, dried (Na₂SO₄), filtered and evaporated in vacuo. The residual amorphous solid was used directly in the next step without further purification.

Step G: Preparation of N-[(1S,3R,4R)-3-(4-chlorophenyl)-4-({4-cyclohexyl-4-[(4,4-dimethyl-2-oxo-1,3-oxazolidin-3-yl)methyl]piperidin-1-yl}carbonyl)cyclopentyl]-N-methyl-2,4-dinitrobenzenesulfonamide A 25 mL round bottom flask equipped with a magnetic stir bar was charged with 0.103 g (0.20 mmol) of the product of Step F, 0.073 g (0.28 mmol) of N-methyl-2,4-dinitrobenzenesulfonamide and 0.157 g (0.60 mmol) of triphenylphosphine. The solids were dissolved in 2 mL of benzene, and the atmosphere in the flask was evacuated and purged with nitrogen. The reaction mixture was stirred and cooled to 0° C. with an external ice-water bath and then 95 μL (0.60 mmol) of diethyl azodicarboxylate was added. The reaction mixture was allowed to warm to room temperature and was stirred an additional 1 h at which point TLC analysis (75% ethyl acetate-hexanes) indicated consumption of the starting material. The reaction mixture was then evaporated in vacuo and the residue was purified on a Biotage Flash 40i chromatography apparatus (40 g Flash 40S silica gel cartridge) eluted with 50% ethyl acetate-hexanes. Evaporation of the purified fractions and drying in vacuo afforded the title compound as an amorphous yellow solid.

Step H: Preparation of 3-[(1-{[(1R,2R,4S)-2-(4-chlorophenyl)-4-(methylamino)cyclopentyl]carbonyl}-4-cyclohexylpiperidin-4-yl)methyl]-4,4-dimethyl-1,3-oxazolidin-2-one A 10 mL round bottom flask equipped with a magnetic stir bar was charged with 0.184 g (0.24 mmol) of the product of Step G dissolved in 2 mL of methylene chloride and the reaction mixture was stirred at room temperature. Propylamine (50 μL, 0.49 mmol) was added via syringe and the reaction mixture developed an intense yellow color. Stirring was continued an additional 15 min, at which point TLC analysis (75% ethyl acetate-hexanes) revealed complete reaction of the starting material. The reaction mixture was concentrated in vacuo, and the residue was applied to two 1000 micron preparative TLC plates. Elution of the plates with a mixture of methylene chloride-methanol-14.8 N aqueous ammonium hydroxide (90:9:1) followed by recovery of the product band from the silica gel afforded 0.040 g of the title compound.

Step I: Preparation of 3-[(1-{[(1R,2R,4S)-2-(4-chlorophenyl)-4-(dimethylamino)cyclopentyl]carbonyl}-4-cyclohexylpiperidin -4-yl)methyl]-4,4-dimethyl-1,3-oxazolidin-2-one A 10 mL round bottom flask equipped with a magnetic stir bar was charged with 0.031 g (0.06 mmol) of the product of Step H dissolved in 1.5 mL methanol and 0.5 mL tetrahydrofuran followed by addition of 0.031 g of finely powdered 4 Å molecular sieves, 0.031 g of paraformaldehyde, 67 μL (1.17 mmol) of acetic acid and 0.020 g (0.32 mmol) of sodium cyanoborohydride. The reaction mixture was stirred 18 h then filtered through a plug of celite® filter aid eluted with excess methylene chloride. The filtrate was washed sequentially with saturated aqueous sodium bicarbonate and brine, then dried (Na₂SO₄), filtered and evaporated in vacuo. The residue was purified on a Gilson model 215 HPLC system using a YMC Pack Pro C18 column (100×20 mm I.D. S-5 μm, 120 Å) gradient eluted with water-acetonitrile containing 0.1% trifluoroacetic acid. Lyophilization of the purified fractions afforded the trifluoroacetic acid salt of the title compound as a white powder [(MS: m/z (MH+)].

Following the procedures in Examples 43 and 44 described above, the following compounds can be prepared:

| Ex. # | stereo. (1, 2, 4) | R¹ | R² | R³ | Parent Ion m/z |
|---|---|---|---|---|---|
| 45 | (R, R, RS) | H-N-Me | —H | —Cl | 530 |
| 46 | (S, S, RS) | H-N-Me | —H | —Cl | 530 |

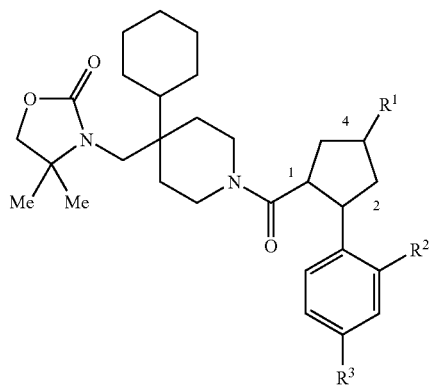

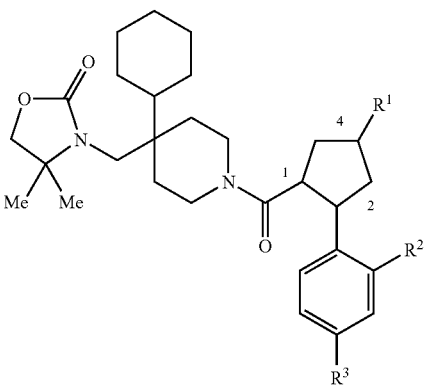

| Ex. # | stereo. (1, 2, 4) | R¹ | R² | R³ | Parent Ion m/z |
|---|---|---|---|---|---|
| 47 | (R, R, R) | MeNH–CH₂– (N-methyl methylamino) | —H | —Cl | 530 |
| 48 | (R, R, S) | MeNH–CH₂– | —H | —Cl | 530 |
| 49 | (R, R, RS) | MeNH–CH₂– | —H | —F | |
| 50 | (R, R, R) | MeNH–CH₂– | —H | —F | |
| 51 | (R, R, R) | MeNH–CH₂– | —F | —F | 532 |
| 52 | (R, R, RS) | MeNH–CH(Me)₂– | —H | —F | |
| 53 | (R, R, R) | MeNH–CH(Me)₂– | —H | —F | |
| 54 | (R, R, R) | MeNH–CH(Me)₂– | —F | —F | 560 |
| 55 | (R, R, RS) | N-methylazetidinyl | —H | —Cl | 556 |
| 56 | (R, R, RS) | N-methylazetidinyl | —H | —F | |
| 57 | (R, R, RS) | N-methylazetidinyl | —F | —F | |
| 58 | (R, R, R) | N-methylazetidinyl | —F | —F | |
| 59 | (R, R, RS) | Me₂N–CH(Me)– | —F | —F | |
| 60 | (R, R, R) | Me₂N–CH(Me)– | —H | —Cl | |
| 61 | (R, R, RS) | Me₂N–CH(Me)– | —H | —F | |
| 62 | (R, R, R) | Me₂N–CH(Me)– | —H | —F | |
| 63 | (R, R, RS) | Me₂N–CH(Me)– | —F | —F | |
| 64 | (R, R, R) | Me₂N–CH(Me)– | —F | —F | |
| 65 | (R, R, RS) | Me₂N–C(Me)₂– | —H | —Cl | 544 |
| 66 | (S, S, RS) | Me₂N–C(Me)₂– | —H | —Cl | 544 |
| 67 | (R, R, R) | Me₂N–C(Me)₂– | —H | —Cl | 544 |
| 68 | (R, R, R) | Me₂N–C(Me)₂– | —H | —F | |

-continued

| Ex. # | stereo. (1, 2, 4) | R¹ | R² | R³ | Parent Ion m/z |
|---|---|---|---|---|---|
| 69 | (R, R, R) | CH₂N(Me)Me | —F | —F | 547 |
| 70 | (R, R, R) | CH₂NH₂ | —H | —F | |
| 71 | (R, R, R) | CH₂NH₂ | —F | —F | 518 |
| 72 | (R, R, R) | CH₂NHCH₂Me | —H | —F | |
| 73 | (R, R, R) | CH₂NHCH₂Me | —F | —F | 547 |

Following procedures similar to that described above, the following compounds can be prepared:

| Ex. # | X | R | Parent Ion m/z |
|---|---|---|---|
| 74 | (iPr)(Me)S(O)₂N(Et) | 4-Cl-phenyl-cyclohexyl-NMe₂ | |
| 75 | Me₃C-NH-C(O)-CH₂ | (4-F-phenyl)-methyl-cyclopentyl-NHMe | |
| 76 | Me₃C-NH-C(O)-CH₂ | (4-F-phenyl)-methyl-cyclopentyl-N(Me)Me | |
| 77 | Me₃C-NH-C(O)-CH₂ | (2,4-diF-phenyl)-methyl-cyclopentyl-NHMe | |

-continued

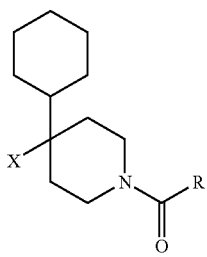

| Ex. # | X | R | Parent Ion m/z |
|---|---|---|---|
| 78 | 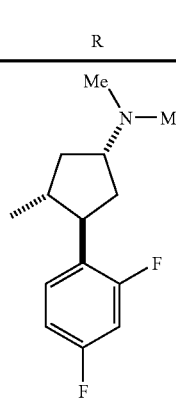 | 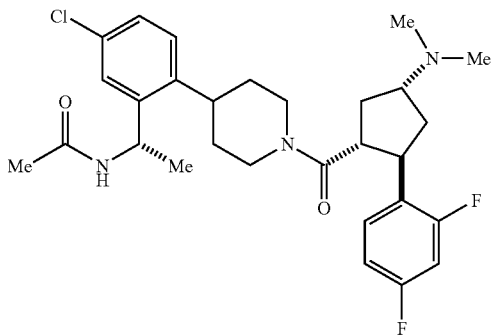 | |

EXAMPLE 79

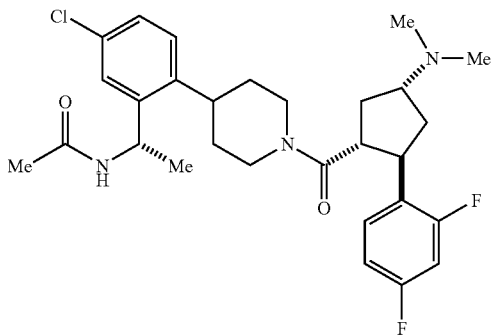

N-{(1S)-1-[5-chloro-2-(1-{[(1R,2R,4R)-2-(2,4-difluorophenyl)-4-(dimethylamino)cyclopentyl]carbonyl}piperidin-4-yl)phenyl]ethyl}acetamide Step A: Preparation of 2-bromo-5-chloro-N-methoxy-N-methylbenzamide N,N-diisopropylethylamine (1.10 mL, 6.36 mmol) was added to a stirred solution of 2-bromo-5-chlorobenzoic acid (0.500 g, 2.12 mmol), N,O-dimethylhydroxyl-amine.HCl (0.310 g, 3.18 mmol), and O-(7-azabenzotriazol-1-yl)-1,1,3,3-tetramethyluronium hexafluoro-phosphate (1.21 g, 3.18 mmol) in N,N-dimethylformamide (8.5 mL) at ambient temperature. After 3 h, the reaction mixture was poured into water and extracted three times with ethyl acetate. The combined organic extracts were washed with saturated aqueous sodium bicarbonate, brine, dried ($MgSO_4$) and concentrated in vacuo. Purification of the crude residue by flash chromatography on silica gel (gradient elution; 0-25% ethyl acetate/hexanes as eluent) gave the title compound as a colorless solid.

Step B: Preparation of 1-(2-bromo-5-chlorophenyl)ethanone

Methylmagnesium bromide (4.26 mL of a 1.4M solution in tetrahydrofuran/toulene, 5.97 mmol) was added dropwise to a stirred solution of 2-bromo-5-chloro-N-methoxy-N-methyl-benzaminde (0.554 g, 1.99 mmol) in tetrahydrofuran (20 mL) at approximately 0° C. After 1 h, 1N hydrochloric acid (5 mL) was added and the resulting biphasic mixture was stirred vigorously for about 10 min. The reaction mixture was poured into water and extracted three times with ethyl acetate. The combined organic extracts were washed with brine, dried ($MgSO_4$) and concentrated in vacuo. Purification of the crude residue by flash chromatography on silica gel (gradient elution; 0-10% ethyl acetate/hexanes as eluent) provided the title compound as a colorless oil.

Step C: Preparation of (1R)-1-(2-bromo-5-chlorophenyl)ethanol

Trimethylborate (1.74 mL, 15.4 mmol) was added to a stirred solution of (S)-(-)-alpha,alpha-diphenyl-2-pyrrolidinemethanol (3.24 g, 12.8 mol) in tetrahydrofaran (350 mL) at room temperature. After 1.25 h, borane-methyl sulfide complex (70.4 mL of a 2M solution in tetrahydrofuran, 0.141 mol) was added slowly and a gentle effervesence was observed. The resulting soution was cooled to approximately 0° C. and a solution of 1-(2-bromo-5-chlorophenyl)ethanone (~30.0 g, 0.128 mmol) in tetrahydrofuran (150 mL) was then added uniformly over 1 h. After the addition, the resulting mixture was allowed to warm to ambient temperature and aged overnight. The reaction mixture was concentrated under reduced pressure to approximately one quarter of its original volume, poured into 1N hydrochloric acid and extracted three times with ethyl acetate. The combined organic extracts were washed with brine, dried ($MgSO_4$) and concentrated in vacuo. Purification of the crude residue by flash chromatography on silica gel (9% ethyl acetate/hexanes as eluent) afforded the title compound as a colorless solid (98:2 enantiomer ratio).

Step D: Preparation of tert-butyl 4-{4-chloro-2-[(1R)-1-hydroxyethyl]phenyl}-3,6-dihydropyridine-1(2H)-carboxylate A vigorously stirred mixture of tert-butyl 4-(4,4,5,5-tetramethyl-1,2,3-dioxaborolan-2-yl)-3,6-dihydropyridine-1(2H)-carboxylate (1-2) (34.0 g, 0.110 mol), (1R)-1-(2-bromo-5chlorophenyl)ethanol (3-4) (25.8 g, 0.110 mmol), potassium phosphate tribasic (70.0 g, 0.330 mol) and tetrakis(triphenylphosphine)palladium(0) (2.54 g, 2.20 mmol) in N,N-dimethylformamide (440 mL) was degassed via three vacuum/nitrogen ingress cycles and then heated at 100° C. for approximately 18 h. After cooling to room temperature, the reaction mixture was poured into ice/water (~1:1) and extracted three times with ethyl acetate. The combined organic extracts were washed with brine, dried ($MgSO_4$) and concentrated in vacuo. Purification of the crude residue by flash chromatography on silica gel (25% ethyl acetate/hexanes as eluent) gave the title compound as a pale yellow foam.

Step E: Preparation of tert-butyl 4-{4-chloro-2-[(1S)-1-(azido)ethyl]phenyl}-3,6-dihydropyridine-1-carboxylate A solution of diethyl azodicarboxylate (49.6 mL, 0.315 mol) was added dropwise to a stirred mixture of tert-butyl 4-{4-chloro-2-[(1R)-1-hydroxyethyl]phenyl}-3,6-dihydropyridine-1(2H)-carboxylate (26.7 g, 78.9 mmol), $Zn(N_3)_2$.2Py (prepared according to: Viaud, M-C; Rollin, P. *Synthesis* 1990:130-131) (48.5 g, 0.158 mol), triphenylphosphine (82.7 g, 0.315 mol) and imidazole (21.5 g, 0.315 mol) in dichloromethane at approximately 0° C. After the addition, the resulting mixture was allowed to warm to ambient temperature and stirred vigorously for 3 days. The reaction mixture was filtered through a short column of silica gel eluted with the appropriate volume of dichloromethane to remove excess salts and polar byproducts. The filtrate was concentrated in vacuo and the crude residue was purified by flash chromatography on silica gel (12.5% ethyl acetate/hexanes as eluent) to furnish the title compound as a viscous pale yellow oil.

Step F: Preparation of tert-butyl 4-{2-[(1S)-1-aminoethyl]-4-chlorophenyl}piperidine-1-carboxylate A mixture of tert-butyl 4-{4-chloro-2-[(1S)-1-(azido) ethyl]phenyl}-3,6dihydropyridine-1-carboxylate (22.9 g, 63.1 mmol) and platinum (IV) oxide (1.08 g, 4.73 mmol) in ethanol/glacial acetic acid (1:1, 200 mL) was hydrogenated at atmospheric pressure for approximately 15 h. The resulting mixture was degassed via three vacuum/hydrogen ingress cycles to remove the liberated nitrogen and the hydrogenation was then continued for a further 24 h. The reaction mixture was filtered through a short column of celite®, the filtrate evaporated and the residue partitioned between methylene chloride and 1N sodium hydroxide. The organic phase was separated and the aqueous phase was re-extracted twice with methylene chloride. The combined organic extracts were washed with water, brine, dried ($Na_2SO_4$), and concentrated in vacuo to give crude (~70% pure) title compound as a colorless foam.

Step G: Preparation of tert-butyl 4-{2-[(1S)-1-(acetylamino) ethyl]-4-chlorophenyl}piperidine-1-carboxylate Acetyl chloride (1.71 mL, 24.0 mmol) was added to a solution crude tert-butyl 4-{2-[(1S)-1-aminoethyl]-4-chlorophenyl}piperidine-1-carboxylate (5.42 g of ~70% pure material, 11.2 mmol) and triethylamine (6.69 mL, 48.0 mmol) in methylene chloride at approximately 0° C. After 2 h, the reaction mixture was poured into water and extracted three times with ethyl acetate. The combined organic extracts were washed with brine, dried ($MgSO_4$) and concentrated in vacuo. Purification of the crude residue by flash chromatography on silica gel (gradient elution; 35-50% ethyl-acetate/hexanes as eluent) provided tert-butyl 4-{2-[(1S)-1-(acetylamino)ethyl]-4-chlorophenyl}piperidine-1-carboxylate as a pale yellow foam. If desired, traces of the minor R-enantiomer could be removed using preparative chiral high pressure liquid chromatography on CHIRALPAK AD Phase (7.5% ethanol/heptanes as eluent) to give in order of elution: R-enantiomer as a colorless solid followed by the S-enantiomer as a colorless solid.

Step H: Preparation of N-[(1S)-1-(5-chloro-2-piperidin-4-ylphenyl)ethyl]acetamide hydrochloride A saturated solution of hydrogen chloride in ethyl acetate (15 mL) was added to a stirred solution of tert-butyl 4-{2-[(1S)-1-(acetylamino)ethyl]-4-chlorophenyl}piperidine-1-carboxylate (3.66 g, 9.61 mmol) in methylene chloride (15 mL) at 0° C. After 3 h, the volatiles were evaporated in vacuo, and the crude residue triturated twice with dry diethyl ether to give the title compound as a colorless solid.

Step I: N-{(1S)-1-[5-chloro-2-(1-{[(1R,2R,4R)-2-(2,4-difluorophenyl)-4-(dimethylamino)cyclopentyl]carbonyl}piperidin-4-yl)phenyl]ethyl}acetamide N,N-diisopropylethylamine (82.4 µL, 0.473 mmol) was added to a stirred suspension of (1R,2R,4R)-2-(2,4-difluorophenyl)-4-(dimethylamino)cyclopentanecarboxylic acid hydrochloride (48.2 mg, 0.158 mmol, prepared essentially as described in EXAMPLE 44), N-[(1S)-1-(5-chloro-2-piperidin-4-ylphenyl)ethyl]acetamide hydrochloride (50 mg, 0.158 mmol), and O-(7-azabenzotriazol-1-yl)-1,1,3,3-tetramethyluronium hexafluorophosphate (72.0 mg, 0.189 mmol) in N,N-dimethylformamide (1.5 mL) at ambient temperature. After approximately 18 h, the reaction mixture was poured into water and extracted three times with ethyl acetate. The combined organic extracts were washed with brine, dried ($Na_2SO_4$) and concentrated in vacuo. Purification of the crude residue by preparative reversed phase high pressure liquid chromatography on YMC Pack Pro C18 phase (gradient elution; 0-100% acetonitrile/water as eluent, 0.1% TPA modifier) afforded the title compound as a buff white solid (m/z (ES) 532 (MH$^+$).

BIOLOGICAL ASSAYS

A. Binding Assay. The Membrane Binding Assay was Used to Identify Competitive Inhibitors of $^{125}$I-NDP-alpha-MSH Binding to Cloned Human MCRs Expressed in Mouse L- or Chinese Hamster Ovary (CHO)-cells.

Cell lines expressing melanocortin receptors were grown in T-180 flasks containing selective medium of the composition: 1 L Dulbecco's modified Eagles Medium (DMEM) with 4.5 g L-glucose, 25 mM Hepes, without sodium pyruvate, (Gibco/BRl); 100 ml 10% heat-inactivated fetal bovine serum (Sigma); 10 mL 10,000 unit/mL penicillin & 10,000 µg/mL streptomycin (Gibco/BRl); 10 ml 200 mM L-glutamine (Gibco/BRl); 1 mg/mL geneticin (G418) (Gibco/BRl). The cells were grown at 37° C. with $CO_2$ and humidity control until the desired cell density and cell number was obtained.

The medium was poured off and 10 mls/monolayer of enzyme-free dissociation media (Specialty Media Inc.) was added. The cells were incubated at 37° C. for 10 min or until cells sloughed off when flask was banged against hand.

The cells were harvested into 200 mL centrifuge tubes and spun at 1000 rpm, 4° C., for 10 min. The supernatant was discarded and the cells were resuspended in 5 mls/monolayer membrane preparation buffer having the composition: 10 mM Tris pH 7.2-7.4; 4 µg/mL Leupeptin (Sigma); 10 µM Phosphoramidon (Boehringer Mannheim); 40 µg/mL Bacitracin (Sigma); 5 µ/mL Aprotinin (Sigma); 10 mM Pefabloc (Boehringer Mannheim). The cells were homogenized with motor-driven dounce (Talboy setting 40), using 10 strokes and the homogenate centrifuged at 6,000 rpm, 4° C., for 15 min.

The pellets were resuspended in 0.2 mls/monolayer membrane prep buffer and aliquots were placed in tubes (500-1000 µL/tube) and quick frozen in liquid nitrogen and then stored at −80° C.

Test compounds or unlabelled NDP-α-MSH was added to 100 µL of membrane binding buffer to a final concentration of 1 µM. The membrane binding buffer had the composition: 50 mM Tris pH 7.2; 2 mM $CaCl_2$; 1 mM $MgCl_2$; 5 mM KCl; 0.2% BSA; 4 µg/mL Leupeptin (SIGMA); 10 µM Phosphoramidon (Boehringer Mannheim); 40 µg/mL Bacitracin (SIGMA); 5 µg/mL Aprotinin (SIGMA); and 10 mM Pefabloc (Boehringer Mannheim). One hundred µL of membrane binding buffer containing 10-40 µg membrane protein was added, followed by 100 µM 125I-NDP-α-MSH to final concentration of 100 pM. The resulting mixture was vortexed briefly and incubated for 90-120 min at room temp while shaking.

The mixture was filtered with Packard Microplate 196 filter apparatus using Packard Unifilter 96-well GF/C filter with 0.1% polyethyleneimine (Sigma). The filter was washed (5 times with a total of 10 mL per well) with room temperature of filter wash having the composition: 50 mM Tris-HCl pH 7.2 and 20 mM NaCl. The filter was dried, and the bottom sealed and 50 µL of Packard Microscint-20 was added to each well. The top was sealed and the radioactivity quantitated in a Packard Topcount Microplate Scintillation counter.

B. Functional Assay. Functional Cell Based Assays were Developed to Discriminate Melanocortin Receptor Agonists from Antagonists.

Cells (for example, CHO- or L-cells or other eukaryotic cells) expressing a human melanocortin receptor (see e.g. Yang-Y K; Ollmann-M M ; Wilson-B D; Dickinson-C; Yamada-T; Barsh-G S; Gantz-I. ; Mol-Endocrinol. 1997 March; 11(3): 274-80) were dissociated from tissue culture flasks by rinsing with Ca and Mg free phosphate buffered saline (14190-136, Life Technologies, Gaithersburg, Md.) and detached following 5 min incubation at 37° C. with enzyme free dissociation buffer (S-014-B, Specialty Media, Lavellette, N.J.). Cells were collected by centrifugation and resuspended in Earle's Balanced Salt Solution (14015-069, Life Technologies, Gaithersburg, Md.) with additions of 10 mM HEPES pH 7.5, 5 mM $MgCl_2$, 1 mM glutamine and 1 mg/ml bovine serum albumin. Cells were counted and diluted to 1 to $5 \times 10^6$/mL. The phosphodiesterase inhibitor 3-isobutyl-1-methylxanthine was added to cells to 0.6 mM.

Test compounds were diluted in dimethylsulfoxide (DMSO) ($10^{-5}$ to $10^{-10}$ M) and 0.1 volume of compound solution was added to 0.9 volumes of cell suspension; the final DMSO concentration was 1%. After room temperature incubation for 45 min, cells were lysed by incubation at 100° C. for 5 min to release accumulated cAMP.

cAMP was measured in an aliquot of the cell lysate with the Amersham (Arlington Heights, Ill.) cAMP detection assay (RPA556). The amount of cAMP production which resulted from an unknown compound was compared to that amount of cAMP produced in response to alpha-MSH which was defined as a 100% agonist. The $EC_{50}$ is defined as the compound concentration which results in half maximal stimulation, when compared to its own maximal level of stimulation.

Antagonist Assay: Antagonist activity was defined as the ability of a compound to block cAMP production in response to alpha-MSH. Solution of test compounds and suspension of receptor containing cells were prepared and mixed as described above; the mixture was incubated for 15 min, and an EC50 dose (approximately 10 nM alpha-MSH) was added to the cells. The assay was terminated at 45 min and cAMP quantitated as above. Percent inhibition was determined by comparing the amount of cAMP produced in the presence to that produced in the absence of test compound.

C. In vivo Food Intake Models.

1) Overnight food intake. Sprague Dawley rats are injected intracerebroventricularly with a test compound in 400 nL of 50% propylene glycol/artificial cerebrospinal fluid one hour prior to onset of dark cycle (12 hours). Food intake is determined using a computerized system in which each rat's food is placed on a computer monitored balance. Cumulative food intake for 16 h post compound administration is measured.

2) Food intake in diet induced obese mice. Male C57/B16J mice maintained on a high fat diet (60% fat calories) for 6.5 months from 4 weeks of age are dosed intraperitoneally with test compound. Food intake and body weight are measured over an eight day period. Biochemical parameters relating to obesity, including leptin, insulin, triglyceride, free fatty acid, cholesterol and serum glucose levels are determined.

D. Rat Ex Copula Assay

Sexually mature male Caesarian Derived Sprague Dawley (CD) rats (over 60 days old) are used with the suspensory ligament surgically removed to prevent retraction of the penis back into the penile sheath during the ex copula evaluations. Animals receive food and water ad lib and are kept on a normal light/dark cycle. Studies are conducted during the light cycle.

1) Conditioning to Supine Restraint for Ex Copula Reflex Tests. This conditioning takes ~4 days. Day 1, the animals are placed in a darkened restrainer and left for 15-30 minutes. Day 2, the animals are restrained in a supine position in the restrainer for 15-30 minutes. Day 3, the animals are restrained in the supine position with the penile sheath retracted for 15-30 minutes. Day 4, the animals are restrained in the supine position with the penile sheath retracted until penile responses are observed. Some animals require additional days of conditioning before they are completely acclimated to the procedures; non-responders are removed from further evaluation. After any handling or evaluation animals are given a treat to ensure positive reinforcement.

2) Ex Copula Reflex Tests. Rats are gently restrained in a supine position with their anterior torso placed inside a cylinder of adequate size to allow for normal head and paw grooming. For a 400-500 gram rat, the diameter of the cylinder is approximately 8 cm. The lower torso and hind limbs are restrained with a non-adhesive material (vetrap). An additional piece of vetrap with a hole in it, through which the glans penis will be passed, is fastened over the animal to maintain the preputial sheath in a retracted position. Penile responses will be observed, typically termed ex copula genital reflex tests. Typically, a series of penile erections will occur spontaneously within a few minutes after sheath retraction. The types of normal reflexogenic erectile responses include elongation, engorgement, cup and flip. An elongation is classified as an extension of the penile body. Engorgement is a dilation of the glans penis. A cup is defined as an intense erection where the distal margin of the glans penis momentarily flares open to form a cup. A flip is a dorsiflexion of the penile body.

Baseline and or vehicle evaluations are conducted to determine how and if an animal will respond. Some animals have a long duration until the first response while others are non-responders altogether. During this baseline evaluation latency to first response, number and type of responses are recorded. The testing time frame is 15 minutes after the first response.

After a minimum of 1 day between evaluations, these same animals are administered the test compound at 20 mg/kg and evaluated for penile reflexes. All evaluations are videotaped and scored later. Data are collected and analyzed using paired 2 tailed t-tests to compared baseline and/or vehicle evaluations to drug treated evaluations for individual animals. Groups of a minimum of 4 animals are utilized to reduce variability.

Positive reference controls are included in each study to assure the validity of the study. Animals can be dosed by a number of routes of administration depending on the nature of the study to be performed. The routes of administration includes intravenous (IV), intraperitoneal (IP), subcutaneous (SC) and intracerebral ventricular (ICV).

E. Models of Female Sexual Dysfunction

Rodent assays relevant to female sexual receptivity include the behavioral model of lordosis and direct observations of copulatory activity. There is also a urethrogenital reflex model in anesthetized spinally transected rats for measuring orgasm in both male and female rats. These and other established animal models of female sexual dysfunction are described in McKenna K E et al, *A Model For The Study of Sexual Function In Anesthetized Male And Female Rats*. Am. J. Physiol. (Regulatory Integrative Comp. Physiol 30):

R1276-R1285, 1991; McKenna K E et al, *Modulation By Peripheral Serotonin of The Threshold For Sexual Reflexes In Female Rats*, Pharm. Bioch. Behav., 40:151-156, 1991; and Takahashi L K et al, *Dual Estradiol Action In The Diencephalon And The Regulation Of Sociosexual Behavior In Female Golden Hamsters*, Brain Res., 359:194-207, 1985.

Representative compounds of the present invention were tested and found to bind to the melanocortin-4 receptor. These compounds were generally found to have $IC_{50}$ values less than 2 μM. Representative compounds of the present invention were also tested in the functional assay and found generally to activate the melanocortin-4 receptor with $EC_{50}$ values less than 1 μM.

EXAMPLES OF A PHARMACEUTICAL COMPOSITION

As a specific embodiment of an oral composition of a composition of the present invention, 5 mg of Example 2 is formulated with sufficient finely divided lactose to provide a total amount of 580 to 590 mg to fill a size O hard gelatin capsule.

As another specific embodiment of an oral composition of a compound of the present invention, 10 mg of Example 79 is formulated with sufficient finely divided lactose to provide a total amount of 580 to 590 mg to fill a size O hard gelatin capsule.

While the invention has been described and illustrated in reference to certain preferred embodiments thereof, those skilled in the art will appreciate that various changes, modifications and substitutions can be made therein without departing from the spirit and scope of the invention. For example, effective dosages other than the preferred doses as set forth hereinabove may be applicable as a consequence of variations in the responsiveness of the mammal being treated for severity of bone disorders caused by resorption, or for other indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention. It is intended, therefore, that the invention be limited only by the scope of the claims which follow and that such claims be interpreted as broadly as is reasonable.

What is claimed is:

1. A compound of structural formula I:

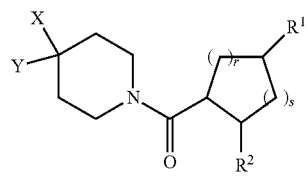

(I)

or a pharmaceutically acceptable salt thereof;
wherein
r is 1 or 2;
s is 1;
n is 0, 1 or 2;
$R^1$ is $NR^6R^7$ wherein $R^6$ and $R^7$ are each independently selected from the group consisting of hydrogen, $C_{1-6}$ alkyl, and $C_{3-6}$ cycloalkyl;
or $R^6$ and $R^7$ together with the nitrogen atom to which they are attached form a 4 membered ring;
$R^2$ is phenyl optionally substituted with one to three groups independently selected from $R^3$;
each $R^3$ is independently selected from the group consisting of hydrogen, halogen, $C_{1-4}$ alkyl, trifluoromethyl, and $C_{1-4}$ alkoxy;
each $R^5$ is independently selected from the group consisting of
hydrogen,
$C_{1-8}$ alkyl;
Y is cyclohexyl, unsubstituted or substituted with one to three groups independently selected from alkyl; and
X is selected from the group consisting of:
$(CH_2)_n$-heterocyclyl,
$(CH_2)_nC(O)N(R^5)(R^5)$, and
$(CH_2)_nNR^5SO_2R^5$,
wherein heterocyclyl is oxazolidinone, optionally substituted with one to three groups independently selected from alkyl.

2. The compound of claim 1 wherein Y is cyclohexyl and X is selected from the group consisting of:
$(CH_2)_n$-heterocyclyl,
$(CH_2)_nC(O)N(R^5)(R^5)$, and
$(CH_2)_nNR^5SO_2R^5$;
wherein heterocyclyl is oxazolidinone, optionally substituted with one to three groups independently selected from alkyl.

3. The compound of claim 1 of structural formula IIa or IIb of the indicated trans relative stereochemical configuration:

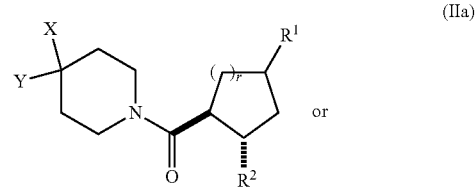

(IIa)

or

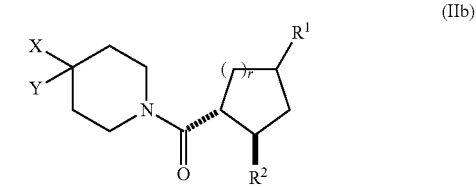

(IIb)

or a pharmaceutically acceptable salt thereof;
wherein
r is 1 or 2;
n is 0, 1, or 2;
p is 0, 1, or 2;
$R^1$ is $NR^6R^7$ wherein $R^6$ and $R^7$ are each independently selected from the group consisting of hydrogen, $C_{1-6}$ alkyl, and $C_{3-6}$ cycloalkyl;
$R^2$ is phenyl optionally substituted with one to three groups independently selected from halogen;
each $R^5$ is independently selected from the group consisting of
hydrogen, and
$C_{1-5}$ alkyl; and
Y represents cyclohexyl.

4. A compound of structural formula IIIa or IIIb of the indicated trans relative stereochemical configuration:

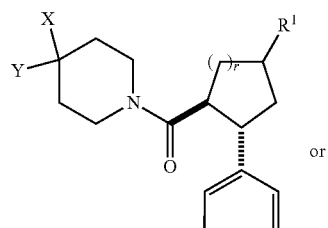
(IIIa)

or

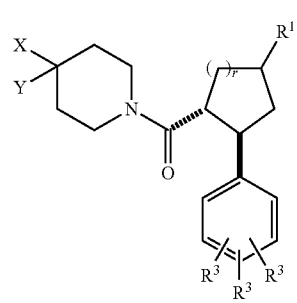
(IIIb)

or a pharmaceutically acceptable salt thereof;
wherein
r is 1 or 2;
$R^1$ is $NR^6R^7$ wherein $R^6$ and $R^7$ are each independently hydrogen, or $C_{1-4}$ alkyl;
each $R^3$ is independently selected from the group consisting of hydrogen, halogen, $C_{1-4}$ alkyl, trifluoromethyl, and $C_{1-4}$ alkoxy;
Y is cyclohexyl; and
X is selected from the group consisting of

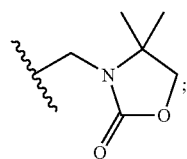 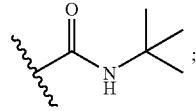

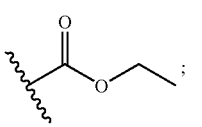 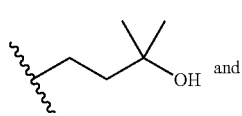 and

-continued

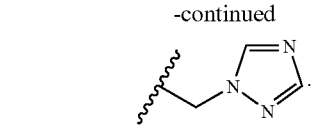

5. A compound selected from the group consisting of:

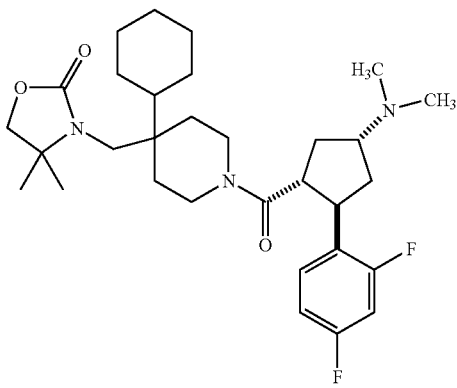

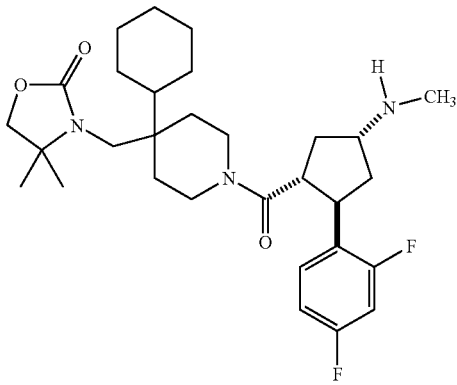

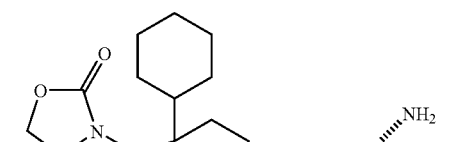

-continued
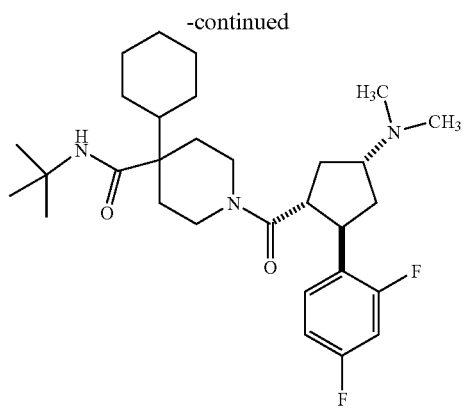
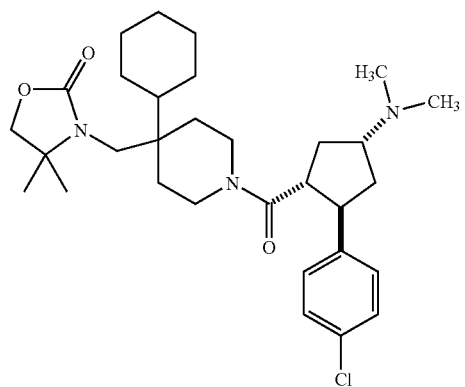
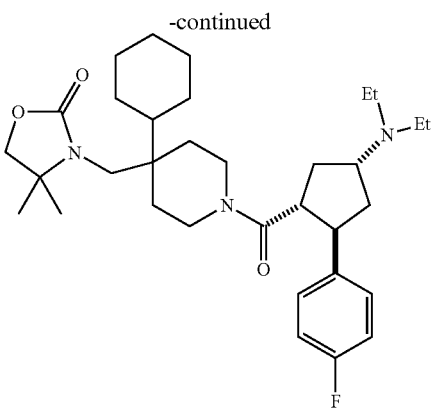
or a pharmaceutically acceptable salt thereof.
6. A pharmaceutical composition which comprises a therapeutically effective amount of a compound of claim 1 and a pharmaceutically acceptable carrier.
* * * * *